(12) United States Patent
O'Donoghue et al.

(10) Patent No.: US 8,119,183 B2
(45) Date of Patent: Feb. 21, 2012

(54) METHOD OF DOPING SURFACES

(75) Inventors: John Gerard O'Donoghue, Dungarvan (IE); Donncha Haverty, Co. Limerick (IE)

(73) Assignee: EnBIO Limited, Carrigtwohill, Co. Cork (IE)

( * ) Notice: Subject to any disclaimer, the term of this patent is extended or adjusted under 35 U.S.C. 154(b) by 1163 days.

(21) Appl. No.: 11/853,764

(22) Filed: Sep. 11, 2007
(Under 37 CFR 1.47)

(65) Prior Publication Data
US 2008/0274671 A1 Nov. 6, 2008

Related U.S. Application Data

(60) Provisional application No. 60/910,464, filed on Apr. 6, 2007.

(51) Int. Cl.
*B05D 3/12* (2006.01)
*B05D 1/12* (2006.01)
*B05D 1/34* (2006.01)
*B05D 5/00* (2006.01)
*B24C 1/00* (2006.01)

(52) U.S. Cl. ........ 427/2.1; 427/2.24; 427/2.25; 427/2.3; 427/180; 427/198; 427/201; 427/299; 427/327; 427/421.1; 427/426; 451/38; 451/39

(58) Field of Classification Search ............... 427/421.1, 427/426, 427, 190, 198, 180, 201, 2.1–2.31, 427/299, 327; 623/11.11; 451/38, 39
See application file for complete search history.

(56) References Cited

U.S. PATENT DOCUMENTS

| 3,754,976 | A | * | 8/1973 | Babecki et al. | 427/192 |
| 4,194,929 | A | * | 3/1980 | Menke | 148/254 |
| 4,214,971 | A | * | 7/1980 | Heikel et al. | 204/290.09 |
| 4,236,940 | A | * | 12/1980 | Manty et al. | 428/472.1 |
| 4,552,784 | A | | 11/1985 | Chu et al. | |
| 4,753,094 | A | | 6/1988 | Spears | |
| 5,607,480 | A | * | 3/1997 | Beaty | 623/23.5 |
| 6,805,750 | B1 | * | 10/2004 | Ristau et al. | 134/1 |

(Continued)

FOREIGN PATENT DOCUMENTS
EP        1395300 A1    3/2004
(Continued)

OTHER PUBLICATIONS

Ishikawa et al. "Blasting Coating Method: New Method of Coating Titanium Surface with Hydroxyapatite at Room Temperature" J. Bio Mat. Res 1997 vol. 38 pp. 129-134.*

(Continued)

*Primary Examiner* — Timothy Meeks
*Assistant Examiner* — Cachet Sellman
(74) *Attorney, Agent, or Firm* — Rissman Hendrickson & Oliverio LLP

(57) ABSTRACT

Disclosed herein are methods of treating an article surface. The method comprises removing a metal oxide surface from the metal substrate to expose a metal surface; and delivering particles comprising a dopant from at least one fluid jet to the metal surface to impregnate the surface of the article with the dopant. The method also comprises delivering substantially simultaneously a first set of particles comprising a dopant and a second set of particles comprising an abrasive from at least one fluid jet to a surface of an article to impregnate the surface of the article with the dopant.

117 Claims, 24 Drawing Sheets

U.S. PATENT DOCUMENTS

| | | |
|---|---|---|
| 6,911,249 B2 | 6/2005 | Wagner et al. |
| 7,377,943 B2 | 5/2008 | Muller et al. |
| 2004/0110021 A1 | 6/2004 | Seth et al. |
| 2004/0158330 A1* | 8/2004 | Muller et al. ............... 623/23.57 |
| 2006/0089270 A1 | 4/2006 | Vose |
| 2006/0219661 A1* | 10/2006 | Towse et al. .................... 216/83 |

FOREIGN PATENT DOCUMENTS

| | | |
|---|---|---|
| GB | 2071521 A | 9/1981 |
| JP | 06330273 A * | 11/1994 |
| WO | WO 96/16611 | 6/1996 |
| WO | WO 9616611 A1 * | 6/1996 |
| WO | WO 03/080140 A1 | 10/2003 |
| WO | WO 2005/074614 A2 | 8/2005 |

OTHER PUBLICATIONS

Alade et al. Hydroxyapatite Waterjet Treatment of Implants. retreived from www.shotpeener.com/library/pdf/2006021.pdf on dated 2006 pp. 6-8.*

AGSCO Corporation. AGSCO Ground Quartz #200 Technical data. retrieved from http://agsco.thomasnet.com/Asset/Quartz%20200.pdf.*

Ishikawa et al, "Blast Coating Method: New Method of Coating Titanium Surface with Hydroxyapatite at Room Tempature", J. Biomed. Mat. Res., 1997, vol. 38 pp. 129-134.

Mano, et al, "Initial tissue response to a titanium implant coated with apatite at room temperature using a blast coating method" 2002, Biomaterials, vol. 23, pp. 1931-1936.

* cited by examiner

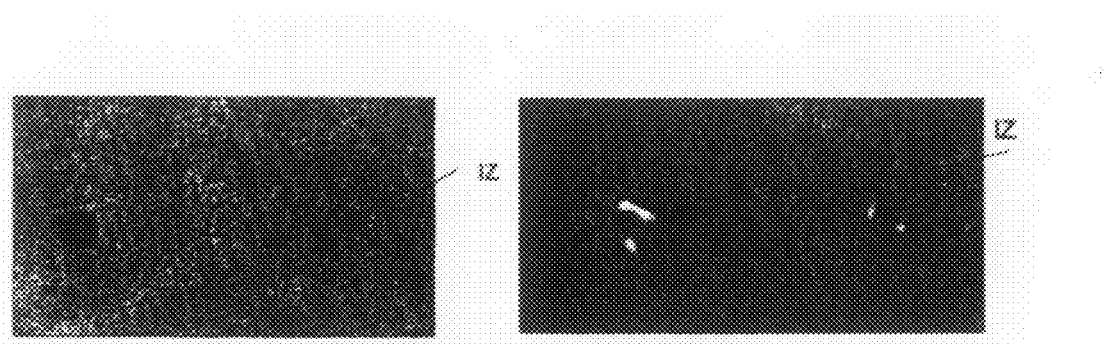
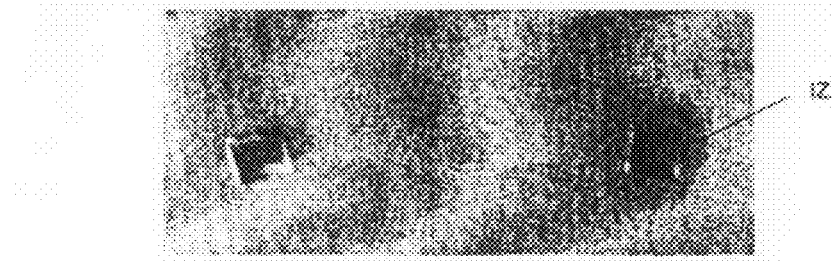
FIG. 8

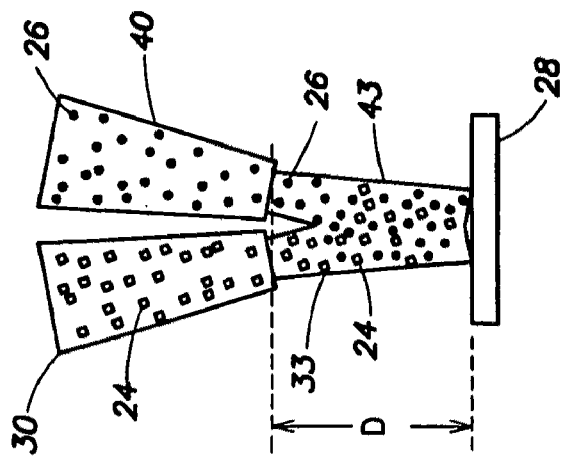
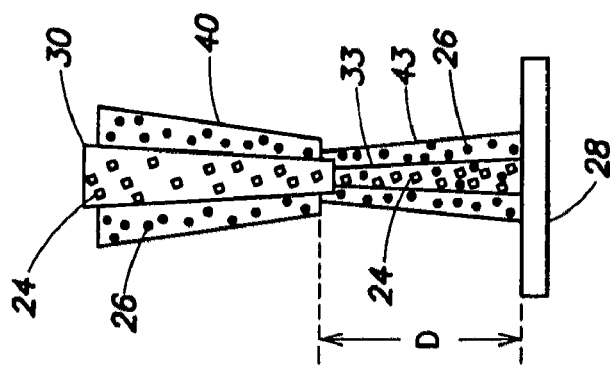
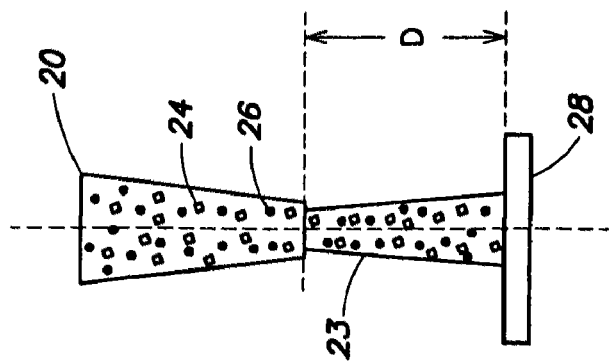

METHOD OF DOPING SURFACES

RELATED APPLICATION

This application claims the benefit of priority under 35 U.S.C. §119(e) to U.S. Provisional Application No. 60/910,464, filed Apr. 6, 2007, the disclosure of which is incorporated herein by reference.

FIELD OF THE INVENTION

The present invention relates to methods of bombarding surfaces of articles, such medical devices, with dopants.

BACKGROUND OF THE INVENTION

The bombardment of metal surfaces with so-called abrasive materials is finding an increasing number of technical applications in recent years. Techniques such as grit blasting, shot blasting, sand blasting, shot peening and micro abrasion fall under this category of surface treatment technique. In each of these techniques, generally, an abrasive material, shot or grit, is mixed with a fluid and delivered at high velocity to impinge the surface to be treated. The technique used to deliver the abrasive material can be classified as wet or dry depending on the choice of fluid medium used to deliver the abrasive to the surface, usually water and air respectively. The generic term "abrasive bombardment" is used to refer to all such techniques in this specification.

Applications of these technologies include metal cutting, cold working metallic surfaces to induce desirable strain characteristics and the pre-treatment of surfaces to induce desirable texture (surface roughness) for the purposes of enhanced adhesion of further coating materials. (See Solomon et al., Welding research, 2003. October: p. 278-287; Momber et al., Tribology International, 2002. 35: p. 271-281; Arola et al., J. Biomed. Mat. Res., 2000. 53(5): p. 536-546; and Arola and Hall, Machining science and technology, 2004. 8(2): p. 171-192.). An example of the latter is to be found in the biomedical sector where titanium implants are grit blasted with alumina or silica to achieve an optimum level of surface roughness that will maximize the adhesion of plasma sprayed hydroxyapatite (HA) coatings on the surface of the implants. HA coated implants are desirable because of the biomimetic properties of the apatite layer but an optimum bonding strength between the titanium surface and the apatite layer is also necessary.

It has been known for some time that during the bombardment of these surfaces some of the abrasive material becomes impregnated in the surface of the metal itself, which has generated some interest in these techniques as possible candidates for modifying surface chemistry in general. (See Arola et al. and Arola and Hall, supra). Again with reference to the biomedical sector one study has looked at shot blasting as a means of putting a hydroxyapatite layer directly on to a titanium surface in an effort to bypass the costly plasma spray process. Ishikawa, K., et al., *Blast coating method: new method of coating titanium surface with Hydroxyapatite at room temperature*. J. Biomed. Mat. Res., 1997. 38: p. 129-134. In this study, HA of an unspecified particle size distribution was used as the abrasive. However, given that the deposited layer of apatite could be removed with a benign washing regime it seems that a strong bond with the surface of the metal was not achieved.

Choi et al. (KR20030078480) refer to the use of a single calcium phosphate particle as a grit blasting media for the purposes of embedding the grit in the surface of dental implants but particle in excess of 190 μm are disclosed.

U.S. Pat. No. 6,502,442 ([6]) refers to the use of sintered HA as the abrasive using water as the fluid medium. Some impregnation of the HA was achieved in this instance as the HA was thermally processed.

Muller et al. (US2004158330) disclosed blasting particles comprising calcium phosphate contained in a glassy matrix. Other disclosures (e.g., U.S. Pat. Nos. 4,752,457 and 6,210,715) describe methods for the manufacture of calcium phosphate micro-spheres usually comprising a polymer component and complex methods of manufacturing the same, but their effectiveness as blasting media was not elucidated.

The Rocatec™ system for the silicization of metallic and other surfaces also uses individual particles having multiple components. This technology is used extensively in the dental arena. In this instance an alumina particle having an outer adherent layer of silica is propelled at a pre-roughened surface and upon impact the local heat generated in the vicinity of the impact causes the shattered silica outer layer to become fused to the surface a process referred to as ceramicization.

Bru-Magniez et al. (U.S. Pat. No. 6,431,958) have disclosed hard abrasive materials with multiple stratified layers for use in blasting abrasive bombardment techniques to modify surfaces. In this instance the purpose of the process was to embed or otherwise attach the stratified layer around the abrasive particles to the surface being treated. The outer layer comprises at least one polymer while the core ceramic material of choice is an oxide, carbide, nitride, or carbonitride.

The use of multiple stratified polymeric layers has been proposed. Lange et al. (U.S. Pat. No. 6,468,658) have disclosed a particle composed of a core base material and an outer adherent layer of titanium dioxide for blasting purposes Further applications of abrasive bombardment for the purposes of surface modification are to be found in the biomedical sector such as for example the use of micro abrasion to clean the oxide slag from the struts of laser machined coronary stents and the impregnation of the surfaces of pacemakers and defibrillators with silica to increase the adhesion of further polymer coatings to the device.

A commonality among these examples is the use of a single type of solid particle in the fluid stream.

The recent significant interest in surface modification technology as it relates to biomedical devices is fueled by the success of the Drug Eluting Stent (DES). Since the introduction of endovascular techniques in the 1990's revascularisation strategies have changed dramatically over the last number of years. However, in-stent restenosis (ISR) remains a problem wherein rupture of the vessel lining at the stent site can cause platelet activation, the secretion of inflammation mediators and eventually smooth muscle cell (SMC) formation, a process analogous to scar formation around a wound site. Furthermore as the stent also contacts the blood it should not induce a foreign body reaction (FBR) in the tissue or blood cells, i.e., it should be biocompatible. The DES uses surface modification technology to combat these problems wherein the surface of the stent is used to deliver active agents (anti-restenosis and anti-thrombosis agents) usually in a polymer matrix locally to the device site where they are most needed. This technology was pioneered by Cordis with there Cypher stent which received FDA approval in 2003. Since then a number of other DES have appeared on the market all aimed at reducing ISR and thrombosis in patients that have percutaneous coronary intervention (PCI) procedures. All of these active devices use a polymer matrix to carry the drug on the surface of the stent and control its elution characteristics in vivo.

However problems have arisen with the DES attributed to a number of factors, among them, achieving proper control of the elution characteristics of the drug(s). The polymer matrix (which degrades with time to release the drug and the polymer degradation products) has been identified as a possible culprit in patients with hypersensitivity. Thus, there are continuing efforts to develop new methods to control the delivery and elution of the drugs.

A large body of prior art in the stent arena has been directed towards achieving passive coatings on the stent surface to mediate ISR. These include such processes as nitriding and carbon-nitriding, the use of carbon and silicon carbide coatings as well as processes to thicken or augment the native oxide layer on the surface of the stent materials including oxidation, ion implantation and electrochemical treatments such as electropolishing or electroplating with inert metals. All such processes however have a number of disadvantages and no one treatment technique as such provides the ideal surface for optimal clinical results.

Another arena of relevance is the area of biofilm formation at the surfaces of implantable devices wherein bacteria at the surface of implant surfaces arrange themselves into films with three dimensional macroscopic structure. In this instance the film itself can represent a barrier to standard antimicrobial treatments such as for example the systemic use of antibiotics. It is reported that the systemic dose of antibiotic required to kill bacterial biofilm infections can be up to 1000 times the systemic dose required to kill their planktonic counterparts in suspension often inducing unwanted and serious side effects in patients. Localized drug delivery at the surfaces of implantable devices has been mentioned as one method to target antimicrobial agents at the implant surface where they are most needed, preventing biofilm formation with the added advantage of using much lower dose rates than systemic treatments.

Currently most bactericidal strategies for localized drug delivery use polymer coatings or polymer micro spheres embedded in other suitable carrier matrices as carriers for antibacterial agents. In addition calcium phosphate salts including hydroxyapatite have been proposed as suitable carriers for antibiotics. Biomimetic deposition has been used to deposit nano crystalline apatite layers on the surfaces of orthopedic metallic implants that can then be loaded with drugs precipitated onto the inorganic coating from solution in a separate step (US20040131754). Such strategies can have dual advantage as for example in the arena of orthopedic implants where the calcium phosphate salt provides an osteo-conductive benefit at the surface inducing bone in-growth in vivo while the antibiotic reduces the risk of biofilm formation, both factors contributing heavily to the need for revision procedures. However this approach is limited by the available surface area at the surface of the implant as this determines the amount of antibiotic that can be loaded. Furthermore the approach is multi-step as often the attachment of the ceramic layer involves high temperature (as for example in the case of plasma sprayed calcium phosphate coatings) or the attachment of the drug requires precise control of the pH and other process parameters precluding the simultaneous attachment of the inorganic salt and the antibacterial agent. Among the antibiotics that have been attached to metal surfaces via such methods are gentamycin, tobramycin, vancomycin, ampicillin, and others.

The range of therapeutic agents that could provide benefit for patients if present at the surface of implants is not limited to antibiotics or immuno-suppressants. Several studies have focused on placing other therapeutic agents at the surface of implantable devices to induce desirable in vivo responses. For example, some studies have focused on placing the functional molecules involved in these cascades at the surfaces of the implants. These include for example proteins among them hormones, growth factors, structural proteins, immunogens and antigens. As a corollary of this much work has focused on the design of peptides and proteins that have structural similarity to the active sites of the proteins involved in biological pathways. For example the use of RGD peptides in orthopedic applications, or bactericidal peptides have been proposed as strategies for combating bacterial infection in instances, e.g., where the bacteria have high resistance to conventional antibiotics.

As medical implants are increasingly tailored to the needs of the patient they can also be viewed as a means to deliver therapeutic agents for the treatment of other more patient specific diseases for example diabetes, cancers and other diseases not directly related to the primary function of the implant. An in vivo device lends itself to multiple functions wherein the surface of the device becomes a vehicle to deliver therapeutic agents that might be required to treat other diseases the patient may have.

The limiting factors in achieving therapeutic agent delivery capacity at the surfaces of implants generally surround the engineering and processing aspects. Methods to put these agents on the surface are required that are commensurate with maintaining the activity and structural integrity of the agents themselves and controlling the surface chemistry particularly there elution kinetics in vivo. As many of the agents desired are biological in nature, temperature and solution parameters such as pH etc can present barriers to realizing the benefit of the above mentioned surface modification strategies.

Surface modification of implant surfaces is not limited to the field of therapeutic agent delivery alone. In many cases surface modification of the implantable device may be required for the purposes of tailoring the physical properties of the surface such as, for example, in titanium based devices used in coronary intervention procedures, and in the treatment of pathological calcifications such as kidney stones. It would, however, be desirable to have devices with higher radio-opacity than that currently associated with these devices in vitro. This would facilitate their radiographic or even magnetic resonance imaging externally and dispense with the need for invasive procedures or endoscopes currently used with minimally invasive procedures. Examples include the doping of nitinol alloys with tertiary heavy elements such as platinum, palladium or tungsten among others to increase the radio opacity of the resulting alloy for biomedical and other applications (U.S. Pat. Nos. 7,128,757, 6,776,795, and 6,569,194).

SUMMARY OF THE INVENTION

The present invention is directed towards providing an improved treatment process for the purposes of modifying the surfaces of articles, such as metallic articles with desirable materials so as to induce at least one of desirable chemical, physical and/or biological characteristics in those surfaces.

One embodiment provides a method of treating a metal substrate, comprising:

removing a metal oxide from a surface of the metal substrate to expose a metal surface; and delivering particles comprising a dopant from at least one fluid jet to the metal surface to impregnate the surface of the substrate with the dopant.

One embodiment provides a method of treating an article surface, the method comprising:

delivering substantially simultaneously a first set of particles comprising a dopant and a second set of particles comprising an abrasive from at least one fluid jet to a surface of an article to impregnate the surface of the article with the dopant.

In other embodiments, the dopant can be polymers, metals, ceramics, therapeutic agents, and combinations thereof. The article can be a medical device, such as an implantable medical device.

BRIEF DESCRIPTION OF THE DRAWINGS

Various embodiments of the invention will be understood from the following description, the appended claims and the accompanying drawings, in which:

FIG. 8 shows bacterial assays of gentamycin/HA treated surfaces for (1) *Staphylococcus aureus*, (2) *Escherichia coli*, and (3) *Pseudomonas aeruginosa* where the left sample for each assay is a negative control, and "IZ" indicates the growth inhibition zone;

FIGS. 9A, 9B, and 9C are schematic diagrams of three different nozzle configurations to deliver the dopants and abrasive to a surface;

FIG. 18 is an AFM (Atomic Force Microscopy) analysis of the thickness of the HA adlayer on the CP titanium surface, where

DETAILED DESCRIPTION

Figure 1:
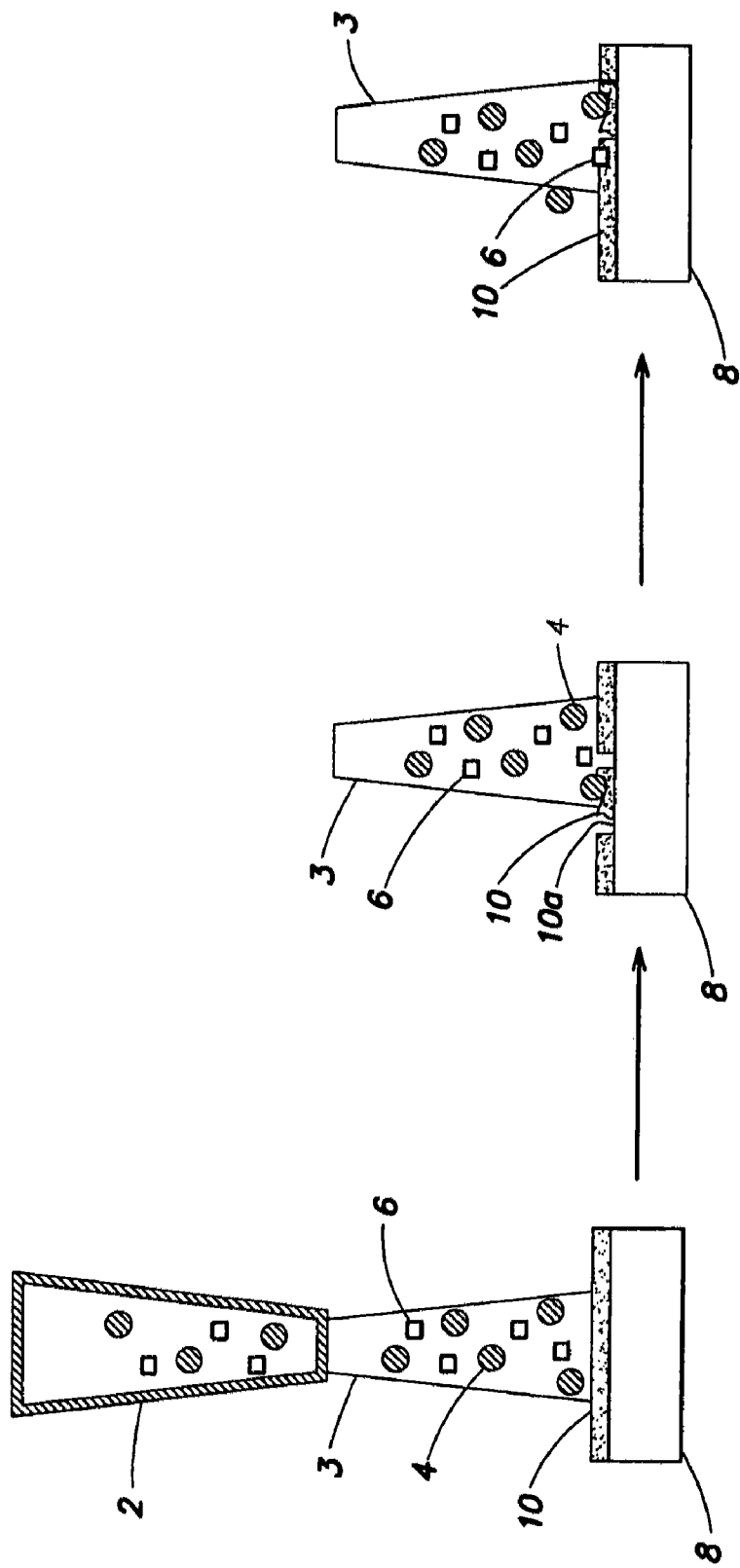
FIG. 1 is a schematic representation of a treatment process of the invention.

One embodiment provides a treatment process of impregnating a surface, such as a metal surface, with a dopant. The strength of the bond between the dopant and the surface and the concentration of dopant achieved in or on the surface can be improved over conventional methods of surface impregnation techniques. The invention relates to dopants that induce desirable chemical, physical and biological properties in the surface of biomedical implants.

Generally the dopant is a material that is incorporated in the bombarded surface but does not extensively impregnate the surface if used as the sole solid component in such a bombardment technique. If the material is delivered to the surface within a high velocity fluid jet on its own, no or minimal surface impregnation will occur. Such circumstances can arise for a number of reasons; the material may not have sufficient particle size or be of sufficient density and hardness to breech the metal surface and impregnate. It may also be a consequence of the nature of the surface itself.

In most metallic materials an oxide layer forms at the surface, which will be harder than the bulk metal or alloy. Metal surfaces (especially those of titanium and titanium derived alloy) are naturally contaminated in air by a variety of contaminants. The detailed physical and chemical properties of any metal surface depend on the conditions under which they are formed. The inherent reactivity of the metal can also attract various environmental chemicals/contaminants that oxidize on the surface. For example, titanium is a highly reactive metal, which is readily oxidized by several different media. This results in titanium always being covered in an oxide layer. This oxide layer is chemically stable but not always chemically inert, as the oxide layer can continue to react with various reactants in its environment, e.g., organic molecules. Traditionally, modification of the titanium surface/oxide layer whereby any new materials in the oxide layer occurred as a by-product of that process. In some cases the new material in the oxide layer can be advantageous to the eventual functionality of the surfaces affected; however, in some cases the new material can constitute an unwanted intrusion. ("Titanium in Medicine," D. M. Brunette; P. Tengvall; M. Textor; P. Thompson, Springer, New York; ISBN 3-540-66936-1.)

The present invention is directed to the intentional addition of a material of choice to the surface. One embodiment takes advantage of the inherent reactivity of metals by the temporary removal of the oxide layer overlying the metal substrate, and treating the newly exposed metal beneath to add a new material (a dopant). Depending on the nature of that added material, the surface properties of the metal article can be tailored according to its intended functional requirements.

Titanium and its alloys always form an oxide layer at the surface. This oxide layer is typically inert and unreactive, while titanium itself is highly reactive and will instantaneously form an oxide layer on exposure to atmospheric environment. Formation of an oxide layer is often a desired property of an implant device.

Examples of dopants in the biomedical device sector includes e.g., hydroxyapatite, drug eluting polymers and other drug delivery systems, and the article to be impregnated comprises a metal such as, e.g., titanium, steel, cobalt chrome and alloys thereof.

Accordingly, one embodiment of the present invention provides a method of treating a metal substrate, comprising:

removing a metal oxide from a surface of the metal substrate to expose a metal surface; and delivering particles comprising a dopant from at least one fluid jet to the metal surface to impregnate the surface of the substrate with the dopant.

In one embodiment, the metal surface is sufficiently reactive in the presence of air that a new oxide layer can form, thus preventing addition of dopant to a metal surface layer. In one embodiment, the present invention involves adding the dopant prior to reoxidation of the newly formed metal surface. In one embodiment, the step of removing the metal oxide surface is performed under an inert atmosphere. In another embodiment, the removing is performed substantially simultaneously with the delivering such that the metal surface is not substantially oxidized prior to the delivering.

The metal oxide layer can be removed by a variety of techniques. In one embodiment, the removing comprises abrasively blasting the metal oxide surface. the step of abrasively blasting in itself can be performed by a number of methods, e.g., grit blasting, micro blasting, water jet blasting, and shot peening, as discussed in further detail below, as well as any other means of abrasive bombardment as known in the art.

In one embodiment, the step of abrasively blasting is performed substantially simultaneously with the step of delivering the particles comprising the dopant, e.g., two streams of particles can be aimed at the metal oxide surface where one stream abrasively blasts the oxide surface to expose the new metal surface and the other stream bombards the new metal surface with dopant.

In another embodiment, the removing is selected from at least one step of drilling, cutting, forming, milling, micromachining, scratching, grinding, polishing, and abrading. In another embodiment, the removing is selected from at least one step of acid etching, alkaline etching, and treating with hydrogen peroxide. In yet another embodiment, the removing comprises a laser treatment selected from ablation, marking/etching, welding, cutting, and cladding. In another embodiment, the removing comprises a plasma treatment selected from etching and cleaning.

As stated above, in certain of the embodiments described herein, the process of the oxide removal may be performed in an inert environment to expose the new metal surface for a sufficient time to conduct the treatment process e.g., the addition of a new material to the surface before re-exposing the surface to an oxygen rich environment. At that time, the oxide layer can regenerate, but influenced/modified by the entrapped added dopant(s).

In one embodiment, equipment for removing the oxide layer prior to or substantially simultaneously with bombarding the surface can be incorporated with the fluid jet as a stand alone unit or can be incorporated into a manufacturing line. The equipment can be used in a point of use setting whereby it would constitute an aseptic surgery based machine that a surgeon could use in an operating room for custom/prescriptive surface modification prior to implantation of the device in the patient. Disposable dopant carrier/filter cartridges can be used to avoid therapeutic cross contamination and ease of cleaning.

If the dopant is delivered simultaneously to the surface with an abrasive impacting with sufficient energy (a material with sufficient particle size, density and hardness) to breech the oxide layer a window of opportunity can be created where the dopant material may be taken up by the surface before the oxide layer reforms around it. The dopant material can become strongly bound within the oxide layer of the surface. Thus, the surface can be impregnated with materials that impart desirable properties to the surface in a cost effective manner at ordinary temperatures. Furthermore the energy dissipated at the impact site of the abrasive may be sufficient for the dopant to become ceramicised or otherwise bonded to the surface. Accordingly, one embodiment provides a method of treating an article surface, the method comprising delivering substantially simultaneously a first set of particles comprising a dopant and a second set of particles comprising an abrasive from at least one fluid jet to a surface of an article to impregnate the surface of the article with the dopant.

One embodiment of the present invention relates to the impregnation of metallic surfaces with a material of choice (here after dopant) using conventional abrasive bombardment techniques by mixing the dopants with an abrasive (shot or grit) material of choice at the surface. The abrasive, impinging the surface with sufficient force to breech the oxide layer or otherwise deform the surface to be treated, creates a window of opportunity wherein the dopant(s) may be taken up by the surface or otherwise incorporated into or onto the surface.

The embodiments of the invention are encompassed in but not limited to the schematic representation of the invention in FIG. 1. FIG. 1 (left) schematically shows a fluid jet (nozzle) 2 that simultaneously delivers a stream 3 comprising a set of abrasive particles 4 and a set of dopant particles 6. Particle sets 4 and 6 bombard a surface 10 of a substrate 8. In one embodiment, the substrate 8 is a metal substrate and the surface 10 is an oxide layer. As a result of bombardment by the abrasive particles 4, the surface oxide layer is disrupted, and breaches in the oxide layer 10 result to expose a new surface 10a of substrate 8 (center). In the case of a metal substrate, the newly exposed surface is a metal surface. As the particle stream 3 continues to impinge substrate 8, the dopant particles 6 (right) are integrated into the surface 10 of substrate 8. Where the substrate is a metal substrate, a new oxide layer 10 reforms around the dopant particles 6.

In certain embodiments, the dopant materials include but are not limited to materials desired at an implant surface for the purposes of steering and improving the body tissue-implant interaction. The dopant can comprise materials such as polymers, metals, ceramics (e.g., metal oxides, metal nitrides), and combinations thereof, e.g., blends of two or more thereof.

Exemplary dopants include, modified calcium phosphates, including $Ca_5(PO_4)_3OH$, $CaHPO_4 \cdot 2H_2O$, $CaHPO_4$, $Ca_8H_2(PO_4)_6 \cdot 5H_2O$, $\alpha\text{-}Ca_3(PO_4)_2$, $\beta\text{-}Ca_3(PO_4)_2$ or any modified calcium phosphate containing carbonate, chloride, fluoride, silicate or aluminate anions, protons, potassium, sodium, magnesium, barium or strontium cations.

Other exemplary dopants include titania ($TiO_2$), zirconia, hydroxyapatite, silica, carbon, and chitosan/chitin.

In one embodiment, the dopant is a combination of an agent-carrying media and at least one therapeutic agent (including biomolecules and biologics). Potential carriers for therapeutic agents including antibiotics, immuno suppressants, antigenic peptides, bactericidal peptides, structural and functional proteins have been disclosed in U.S. Pat. No. 6,702,850). Calcium phosphate coatings as the drug carrier can also be used (see U.S. Pat. Nos. 6,426,114, 6,730,324, and U.S. Provisional Application No. 60/410,307, the disclosures of which are incorporated herein by reference). Dopants that can act as agent-carrying media include nanoporous, mesoporpous, nanotubes, micro-particles of various materials including hydroxyapatite, silica, carbon, and titania ($TiO_2$) capable of carrying therapeutic agents, biomolecules and biologics. Particulates and powders (e.g. titania powder) can be either adhesively bonded or covalently attached (tethered) to the therapeutic agents, biomolecules and biologics.

Composites of media and carriers (e.g. sintered together), and combinations of carriers can convey drugs and biologics and can control elution profiles.

Other exemplary dopants include barium titanate, zeolites (aluminosilicates), including siliceacous zeolite and zeolites containing at least one component selected from phosphorous, silica, alumina, zirconia, calcium carbonate, biocompatible glass, calcium phosphate glass. The dopant can also be a growth factor consisting of epidermal growth factors, transforming growth factor α, transforming growth factor β, vaccinia growth factors, fibroblast growth factors, insulin-like growth factors, platelet derived growth factors, cartilage derived growth factors, interlukin-2, nerve cell growth factors, hemopoietic cell growth factors, lymphocyte growth factors, bone morphogenic proteins, osteogenic factors or chondrogenic factors.

In one embodiment, the dopant is hydroxyapatite deposited on a titanium surface. Both HA and $TiO_2$ constitute excellent biocompatible biointerfaces, both being biostable and safe in the body. Both can be termed bioreactive in that they can induce specific responses in certain tissues particularly bone tissue. The surface resulting from the deposition of HA on titanium as delivered by the micro-blasting technique combines the benefits of both materials. The $TiO_2$ is not fully covered by the dopant (HA) and therefore still presents to the biological tissue, while the HA affixed on and in the surface is not denatured by the deposition process and therefore conveys its full benefit to the surrounding tissue. In this manner the different benefits of both biomaterials can brought to bear in the biointerface and when further combined with the surface texture/morphology best suited to intended functionality of the implant, and moreover the availability of a drug delivery mechanism, can provide various methods for tailoring the therapeutic, compositional and morphological profile available to the patient end user.

In one embodiment, the dopant is a therapeutic agent. The therapeutic agent can be delivered as a particle itself, or immobilized on a carrier material. Exemplary carrier materials include any of the other dopants listed herein (those dopants that are not a therapeutic agent) such as polymers, calcium phosphate, titanium dioxide, silica, biopolymers, biocompatible glasses, zeolite, demineralized bone, de-proteinated bone, allograft bone, and composite combinations thereof.

Exemplary classes of therapeutic agents include anti-cancer drugs, anti-inflammatory drugs, immunosuppressants, an antibiotic, heparin, a functional protein, a regulatory protein, structural proteins, oligo-peptides, antigenic peptides, nucleic acids, immunogens, and combinations thereof.

In one embodiment, the therapeutic agent is chosen from antithrombotics, anticoagulants, antiplatelet agents, thrombolytics, antiproliferatives, anti-inflammatories, antimitotic, antimicrobial, agents that inhibit restenosis, smooth muscle cell inhibitors, antibiotics, fibrinolytic, immunosuppressive, and anti-antigenic agents.

Exemplary anticancer drugs include acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, Bacillus calmette-guerin (BCG), Baker's Antifol (soluble), beta-2'-deoxythioguanosine, bisantrene HCl, bleomycin sulfate, busulfan, buthionine sulfoximine, BWA 773U82, BW 502U83.HCl, BW 7U85 mesylate, ceracemide, carbetimer, carboplatin, carmustine, chlorambucil, chloroquinoxaline-sulfonamide, chlorozotocin, chromomycin A3, cisplatin, cladribine, corticosteroids, Corynebacterium parvum, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, edatrexate, edelfosine, eflornithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, Fluosol®, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, interferon alfa, interferon beta, interferon gamma, interleukin-1 alpha and beta, interleukin-3, interleukin-4, interleukin-6, 4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of Bacillus calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864, zorubicin, and mixtures thereof.

Exemplary therapeutic agents include immunogens such as a viral antigen, a bacterial antigen, a fungal antigen, a parasitic antigen, tumor antigens, a peptide fragment of a tumor antigen, meta static specific antigens, a passive or active vaccine, a synthetic vaccine or a subunit vaccine.

The dopant may be a protein such as an enzyme, antigen, growth factor, hormone, cytokine or cell surface protein.

The dopant may be a pharmaceutical compound such as an anti-neoplastic agent, an anti-bacterial agent, an anti parasitic agent, an anti-fungal agent, an analgesic agent, an anti-inflammatory agent, a chemotherapeutic agent, an antibiotic or combinations thereof.

The dopant could also be growth factors, hormones, immunogens, proteins or pharmaceutical compounds that are part of a drug delivery system such as those immobilized on zeolite or polymeric matrices, biocompatible glass or natural porous apitic templates such as coralline HA, demineralised bone, deproteinated bone, allograft bone, collagen or chitin.

In one embodiment, the dopant is an anti-inflammatory drugs selected from non-steroidal anti-inflammatory drugs, COX-2 inhibitors, glucocorticoids, and mixtures thereof. Exemplary non-steroidal anti-inflammatory drugs include aspirin, diclofenac, indomethacin, sulindac, ketoprofen, flurbiprofen, ibuprofen, naproxen, piroxicam, tenoxicam, tolmetin, ketorolac, oxaprosin, mefenamic acid, fenoprofen, nambumetone, acetaminophen, and mixtures thereof. Exemplary COX-2 inhibitors include nimesulide, NS-398, flosulid, L-745337, celecoxib, rofecoxib, SC-57666, DuP-697, parecoxib sodium, JTE-522, valdecoxib, SC-58125, etoricoxib, RS-57067, L-748780, L-761066, APHS, etodolac, meloxicam, S-2474, and mixtures thereof. Exemplary glucocorticoids are include hydrocortisone, cortisone, prednisone, prednisolone, methylprednisolone, meprednisone, triamcinolone, paramethasone, fluprednisolone, betamethasone, dexamethasone, fludrocortisone, desoxycorticosterone, and mixtures thereof.

Other exemplary therapeutic agents include cell cycle inhibitors in general, apoptosis-inducing agents, antiproliferative/antimitotic agents including natural products such as vinca alkaloids (e.g., vinblastine, vincristine, and vinorelbine), paclitaxel, colchicine, epidipodophyllotoxins (e.g., etoposide, teniposide), enzymes (e.g., L-asparaginase, which systemically metabolizes L-asparagine and deprives cells that do not have the capacity to synthesize their own asparagine); antiplatelet agents such as G(GP) II$_b$/III$_a$ inhibitors, GP-IIa inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), triazenes-dacarbazine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine (cladribine)); platinum coordination complexes (cisplatin, carboplatin), procarbazine, hydroxyurea, mitotane, aminoglutethimide; hormones (e.g., estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fluorocortisone, prednisone, prednisolone, 6α-methylprednisolone, triamcinolone, betamethasone, and dexamethasone), non-steroidal agents (salicylic acid derivatives e.g., aspirin; para-aminophenol derivatives e.g., acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); antigenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retinoid; cyclin/CDK inhibitors; HMG co-enzyme reductase inhibitors (statins); and protease inhibitors (matrix protease inhibitors).

In one embodiment, the dopant is an antibiotic chosen from tobramycin, vancomycin, gentamicin, ampicillin, penicillin, cephalosporin C, cephalexin, cefaclor, cefamandole and ciprofloxacin, dactinomycin, actinomycin D, daunorubicin, doxorubicin, idarubicin, penicillins, cephalosporins, and quinolones, anthracyclines, mitoxantrone, bleomycins, plicamycin (mithramycin), mitomycin, and mixtures thereof.

In one embodiment, the dopant is a protein chosen from albumin, casein, gelatin, lysosime, fibronectin, fibrin, chitosan, polylysine, polyalanine, polycysteine, Bone Morphogenetic Protein (BMP), Epidermal Growth Factor (EGF), Fibroblast Growth Factor (bFGF), Nerve Growth Factor (NGF), Bone Derived Growth Factor (BDGF), Transforming Growth Factor-.beta.1 (TGF-.beta.1), Transforming Growth Factor-.beta. (TGF-.beta.), the tri-peptide arginine-glycine-aspartic acid (RGD), vitamin D3, dexamethasone, and human Growth Hormone (hGH), epidermal growth factors, transforming growth factor α, transforming growth factor β, vaccinia growth factors, fibroblast growth factors, insulin-like growth factors, platelet derived growth factors, cartilage derived growth factors, interlukin-2, nerve cell growth factors, hemopoietic cell growth factors, lymphocyte growth factors, bone morphogenic proteins, osteogenic factors, chondrogenic factors, or and mixtures thereof.

In one embodiment, the dopant is a heparin selected from recombinant heparin, heparin derivatives, and heparin analogues or combinations thereof.

In one embodiment, the dopant is an oligo-peptide, such as a bactericidal oligo-peptide.

In one embodiment, the dopant is an osteoconductive or osteointegrative agent.

In one embodiment, the dopant is an immunosuppressant, such as cyclosporine, rapamycin and tacrolimus (FK-506), ZoMaxx, everolimus, etoposide, mitoxantrone, azathioprine, basiliximab, daclizumab, leflunomide, lymphocyte immune globulin, methotrexate, muromonab-CD3, mycophenolate, and thalidomide.

In one embodiment, the carrier material is a polymer such as polyurethanes, polyethylene terephthalate, PLLA-polyglycolic acid (PGA) copolymer (PLGA), polycaprolactone, poly-(hydroxybutyrate/hydroxyvalerate) copolymer, poly (vinylpyrrolidone), polytetrafluoroethylene, poly(2-hydroxyethylmethacrylate), poly(etherurethane urea), silicones, acrylics, epoxides, polyesters, urethanes, parlenes, polyphosphazene polymers, fluoropolymers, polyamides, polyolefins, and blends and copolymers thereof.

In one embodiment, the dopant is a radio opaque material, such as those chosen from alkalis earth metals, transition metals, rare earth metals, and oxides, sulphates, phosphates, polymers and combinations thereof.

In one embodiment, the carrier material is a biopolymer selected from polysaccharides, gelatin, collagen, alginate, hyaluronic acid, alginic acid, carrageenan, chondroitin, pectin, chitosan, and derivatives, blends and copolymers thereof.

In one embodiment, the dopant is delivered in a gaseous carrier fluid, such as nitrogen, hydrogen, argon, helium, air, ethylene oxide, and combinations thereof. In another embodiment, the dopant is delivered in a liquid carrier fluid. In one embodiment, the liquid is also an etching liquid (basic or acidic) In one embodiment, the dopant is delivered in an inert environment.

Another embodiment relates to the chemical treatment of metal surfaces for the purposes of adhesion. Good adhesion of paints and polymeric coatings to metal surfaces is an area of increasing technical importance. This technology can be used to pre-treat a surface by impregnating it with compounds having desired chemical functionality. These include but are not limited to polymers or silica materials having siloxane groups.

The pretreatment can be used to lay down a very strongly bound layer of seed polymer material on the surface. Further polymer coatings could then be attached to this seed layer rather than trying to attaching it directly to the surface of the metal.

The dopant is not limited to one compound but could be any combination of any of the materials listed or even any material(s) that do(es) not have the necessary mechanical properties to impregnate the surface if delivered singularly at high velocity to the surface.

In one embodiment, the dopant can be any material so long as it is passive, i.e., unreactive with the surface. It simply has to be at the surface when the oxide layer is breeched by the abrasive so that the oxide reforms around it.

In one embodiment, the dopant is nanocrystalline.

In one embodiment, the dopant is nanocrystalline hydroxyapatite.

In one embodiment the abrasive has a suitable property chosen from at least one of size, shape, hardness, and density to break the oxide layer. In one embodiment, the abrasive has a modus hardness ranging from 0.1 to 10, such as a modus hardness ranging from 1 to 10, or a modus hardness ranging from 5 to 10. In another embodiment, the abrasive has a particle size ranging from 0.1 µm to 10000 µm, such as a particle size ranging from 1 µm to 5000 µm, or a particle size ranging from 10 µm to 1000 µm.

Abrasive materials to be used in this invention include but are not limited to shot or grit made from silica, alumina, zirconia, barium titanate, calcium titanate, sodium titanate, titanium oxide, glass, biocompatible glass, diamond, silicon carbide, calcium phosphate, calcium carbonate, metallic powders, carbon fiber composites, polymeric composites, titanium, stainless steel, hardened steel, carbon steel chromium alloys or any combination thereof.

The pressure of the fluid jet will also be a factor in determining the impact energy of the abrasive. The abrasive and dopant(s) do not have to be delivered to the surface through the same jet. They could be in any number of separate jets as long as they deliver the solid components to the surface at the substantially the same time, e.g., prior to reformation of the oxide layer if the surface is a metal. This allows a large amount of flexibility in optimizing the invention towards a specific need. In one embodiment, the fluid jet is selected from wet blasters, abrasive water jet peening machines, and wet shot peening machines. In one embodiment, the at least one fluid jet operates at a pressure ranging from 0.5 to 100 bar, such as a pressure ranging from 1 to 30 bar, or a pressure ranging from 1 to 10 bar.

In another embodiment, the at least one fluid jet is selected from dry shot peening machines, dry blasters, wheel abraders, grit blasters), sand blasters(s), and micro-blasters. In one embodiment, the at least one fluid jet operates at a pressure ranging from 0.5 to 100 bar, such as a pressure ranging from 1 to 30 bar, or a pressure ranging from 3 to 10 bar.

In other embodiments, blasting equipment can be used in conjunction with controlled motion such as CNC or robotic control. The blasting can be performed in an inert environment.

In one embodiment, the dopants and abrasives are contained in the same reservoir and are delivered to a surface from the same jet (nozzle). In another embodiment, the dopant is contained in one reservoir and abrasive contained in a separate reservoir, and multiple nozzles deliver the dopants and abrasives. The multiple nozzles can take the form of a jet within a jet, i.e., the particles from each jet bombard the surface at the same incident angle. In another embodiment, the multiple are spatially separated so as to bombard the surface at different incident angles yet hit the same spot on the surface simultaneously.

FIGS. 9A, 9B, and 9C are schematic diagrams of three different nozzle configurations to deliver the dopants and abrasive to a surface: single nozzle (9A); multiple nozzles with dopants and abrasives delivered from separate reservoirs where one nozzle is situated within another nozzle (9B); and multiple, separate nozzles with dopants and abrasives delivered from separate reservoirs (9C). More specifically, FIG. 9A shows a single nozzle 20 for delivering a single stream 23 of abrasive particles 24 and dopant particles 26 to a substrate 28. FIG. 9B shows that multiple nozzles with dopants and abrasives delivered from separate reservoirs can be used, where FIG. 9B illustrates one nozzle 30 for delivering a stream 33 of abrasive particles 24 situated within another nozzle 40 for delivering a stream 43 of dopant particles 26, where streams 33 and 43 are coaxial. Multiple, separate nozzles with dopants and abrasives delivered from separate reservoirs can also be used, as indicated in FIG. 9C, which shows nozzles 30 and 40, for delivering streams 33 and 43 of abrasive particles 24 and dopant particles 26, respectively.

It can be readily appreciated that where more than one type of dopant is used, dopants can be delivered from a single nozzle, or from separate nozzles. For example, where the dopant combination is a therapeutic agent combined with another particle (e.g., hydroxyapatite), a two nozzle design can be used for delivering the dopant combination from one nozzle and the abrasive from the second nozzle. In another embodiment, a three nozzle configuration can be used where the therapeutic agent is delivered from a first nozzle, the second set of dopant particles is delivered from a second nozzle, and the abrasive is delivered from a third nozzle.

In one embodiment, the article is an implantable medical device. Exemplary medical devices include catheters, guide wires, and baskets used in the removal of pathological calcifications. In the case of biomedical devices it is desirable that the level of impregnation of the abrasive itself in the surface is minimal. The abrasive should further be biocompatible as it is likely that some impregnation will occur.

In one embodiment, the article is a metal, such as those metals chosen from pure metals, metal alloys, intermetals comprising single or multiple phases, intermetals comprising amorphous phases, intermetals comprising single crystal phases, and intermetals comprising polycrystalline phases. Exemplary metals include titanium, titanium alloys (e.g., NiTi or nitinol), ferrous alloys, stainless steel and stainless steel alloys, carbon steel, carbon steel alloys, aluminum, aluminum alloys, nickel, nickel alloys, nickel titanium alloys, tantalum, tantalum alloys, niobium, niobium alloys, chromium, chromium alloys, cobalt, cobalt alloys, precious metals, and precious metal alloys. In one embodiment, the metal is titanium.

In one embodiment the abrasive material is alumina (10 Mesh) while the dopant is HA with a particle size range of 0.1 to 3 μm. The mixed media is achieved by mixing the dopant and abrasive between the ratio of 5:95 and 95:5 HA to Silica volume % but more preferably between the ratio of 80:20 to 20:80 and most preferably in the ratio range 60:40 to 40:60. The silica bead has a Mohs hardness in the range of 0.1 to 10 but most preferably in the range of 2 to 10 and most preferably in the range 5 to 10. This mixed media is delivered to a titanium surface using a standard grit blasting machine operating in the pressure range of 0.5 Bar to 20 Bar, such as a pressure range of 2 to 10 bar, or a pressure range of 4 Bar to 6 Bar. The distance between the nozzle and the surface can be in the range of 0.1 mm to 100 mm, such as a range of 0.1 mm to 50 mm, or a range of 0.1 mm to 20 mm. The angle of the nozzle to the surface can range from 10 degrees to 90 degrees, such as a range of 30 degrees to 90 degrees, or a range of 70 to 90 degrees.

In another embodiment the abrasive material is silica (10 Mesh) while the dopant is HA with a particle size range of 0.1 to 3 μm. The mixed media is achieved by mixing the dopant and abrasive between the ratio of 5:95 and 95:5 HA to alumina weight % but more preferably between the ratio of 80:20 to 20:80 and most preferably in the ratio range 60:40 to 40:60. The Alumina grit has a Mohs hardness in the range of 0.1 to 10, such as a range of 2 to 10, or a range of 5 to 10. This mixed media can be delivered to a titanium surface using a standard grit blasting machine operating in the pressure range 0.5 Bar to 20 Bar, such as a pressure range of 2 to 10 bar, a range of 4 Bar to 6 Bar. The distance between the nozzle and the surface can range from 0.1 mm to 100 mm, such as a range of 0.1 mm to 50 mm, or a range of 0.1 mm to 20 mm. The angle of the nozzle to the surface can range from 10 degrees to 90 degrees, such as a range of 30 degrees to 90 degrees, or a range of 70 to 90 degrees.

One of ordinary skill in the art can appreciate the influence of machine parameters including jet velocity, operating pressure, venturi configuration, angle of incidence and surface to nozzle distances on the extent of impregnation of the dopant in the surface using these mixed media.

One of ordinary skill in the art can appreciate the effect of the size, shape, density and hardness of the abrasive material used on the extent of impregnation of the dopant in the surface using these mixed media.

One of ordinary skill in the art can appreciate the effect of the fluid stream itself, the blasting equipment using a gas medium (typically air) the effects of using inert gases as a carrier fluid e.g. N2 or noble gases such as Ar and He on the extent of impregnation of the dopant in the surface using these mixed media.

In the case of wet blasting equipment using a liquid as a carrier fluid (normally water), One of ordinary skill in the art can appreciate the effect of acidity and basicity on the extent of impregnation of the dopant in the surface using these mixed media.

As disclosed herein, the disclosed methods can be useful for modifying the surfaces of medical devices. In the context of medical device applications, dopants can be active (eliciting a biological response) or passive (not eliciting a biological response). Passive dopants can be conveyed to enhance lubricity or render a substrate radio-opaque, of enhance wear characteristics or enhance adhesion of an ad-layer, etc. Active agents can evoke a response from the host tissue in vivo, enhancing the functionality of the device or the surgery, or delivering a benefit as a secondary function to the device.

The process is a deposition process allowing for the addition of material(s) to a surface by a methodology typically used to remove material from a surface. In one embodiment, the method allows for the impregnation of the surface using:

1. abrasive bombardment to convey an additional material onto and/or into a surface;
2. the removal of oxide layers from a surface in an inert environment and the subsequent deposition of additional material onto or into the surface prior to allowing the surface to oxidise over again; or
3. a combination of 1 and 2 above The process can be used to modify, augment or treat surfaces such as to change surface characteristics/properties including one or more of:
 morphology/topography/form/texture/roughness/microstructure
 surface area
 surface porosity
 structure—order/disorder of molecular assemblies, inclusions, vacancies, and organisation
 crystallinity, size, distribution and orientation of crystals
 chemistry,
 chemical composition,
  elemental composition
  chemical state of elements
  molecular composition
  functional groups
  molecular adlayers
  adventitious contaminants and impurities
 oxide layer porosity, thickness and composition,
 biochemistry
 biological performance
 surface energy—lipophilic/lipophobic properties
 wetabillity—hydrophilic and hydrophobic properties,
 adsorption—physisorption and chemisorption
 electric properties—surface potentials and surface charges, dielectric constant
 magnetic properties
 optical properties—optical reflection/absorption
 surface mechanical properties—Elastic/plastic nature of surface layers, tensile/compressive forces in the surface
 surface dynamic properties—mobility of atoms and molecules The effect on the surface is such as to modify the chemistry and topography of the surface material resulting in an infinite range of manifestations. The desired outcome resulting from the treatment is influenced by:
 the substrate material and its surface characteristics
 the treatment process parameters and the environmental conditions
 the abrasive(s) and its mechanical and chemical properties, size, hardness, morphology etc
 the dopant material(s) and its chemical and mechanical properties, whether it is a carrier medium for additional agents (e.g. therapies), or an active or passive agent, or a composite or a cocktail mix.

In one embodiment, the methods described herein can provide one or more of the following feature
 a room temperature process
  no degradation of the dopant material(s) due to temperature or process
  ability to convey temperature sensitive agents to the surface intact.
 one step process that is manufacturing friendly
 no conformal polymer film required to convey therapeutic agents
 no laminate layer results—cannot be chipped or peeled off
 adaptable to allowing implants to be custom treated for specific applications
 has application in industrial sectors outside the Medical Device sector, e.g., industries that use titanium, e.g., the aerospace sector, the food sector (use of titanium pipes), and the semiconductor sector, etc.

EXAMPLES

Example 1

This example describes the modification of a titanium substrate using hydroxyapatite (HA) as the dopant and alumina bead as the abrasive.

A mixed media was prepared consisting of 50 weight percent alumina (White Saftigrit: Mesh size 150, 88 micron particle size, Mohs hardness 9, Guyson international Ltd) and 50 weight percent HA (Fluka Synthetic hydroxyapatite (Fluka production GmbH, Buchs, Switzerland, part of the Sigma-Aldrich family). A Rocatec™ grit blaster operating at a pressure of 5 bar was used to grit blast a 2 cm×2 cm CP titanium coupon (Titanium Sheet Grade 2 Medical to ASTM F67 Spec.). The nozzle to surface distance was 1 cm and the nozzle was held at 900 to the surface. The silicon carbide nozzle had an orifice diameter of 1 mm and traversed the surface at 2 cm per sec. The surface was subjected to three passes.

Two further samples of Titanium (Titanium Sheet Grade 2 Medical to ASTM F67 Spec.) were subjected to the same treatment but with the media consisting of HA only.

The samples were then subjected to a cleaning treatment involving 20 minutes ultrasonic washing in deionized water to remove any material that was not intimately affixed to the surface. After the ultrasonic cleaning the samples were rinsed with deionized water and air-dried in an oven at 95° C. for one hour.

Figure 2:
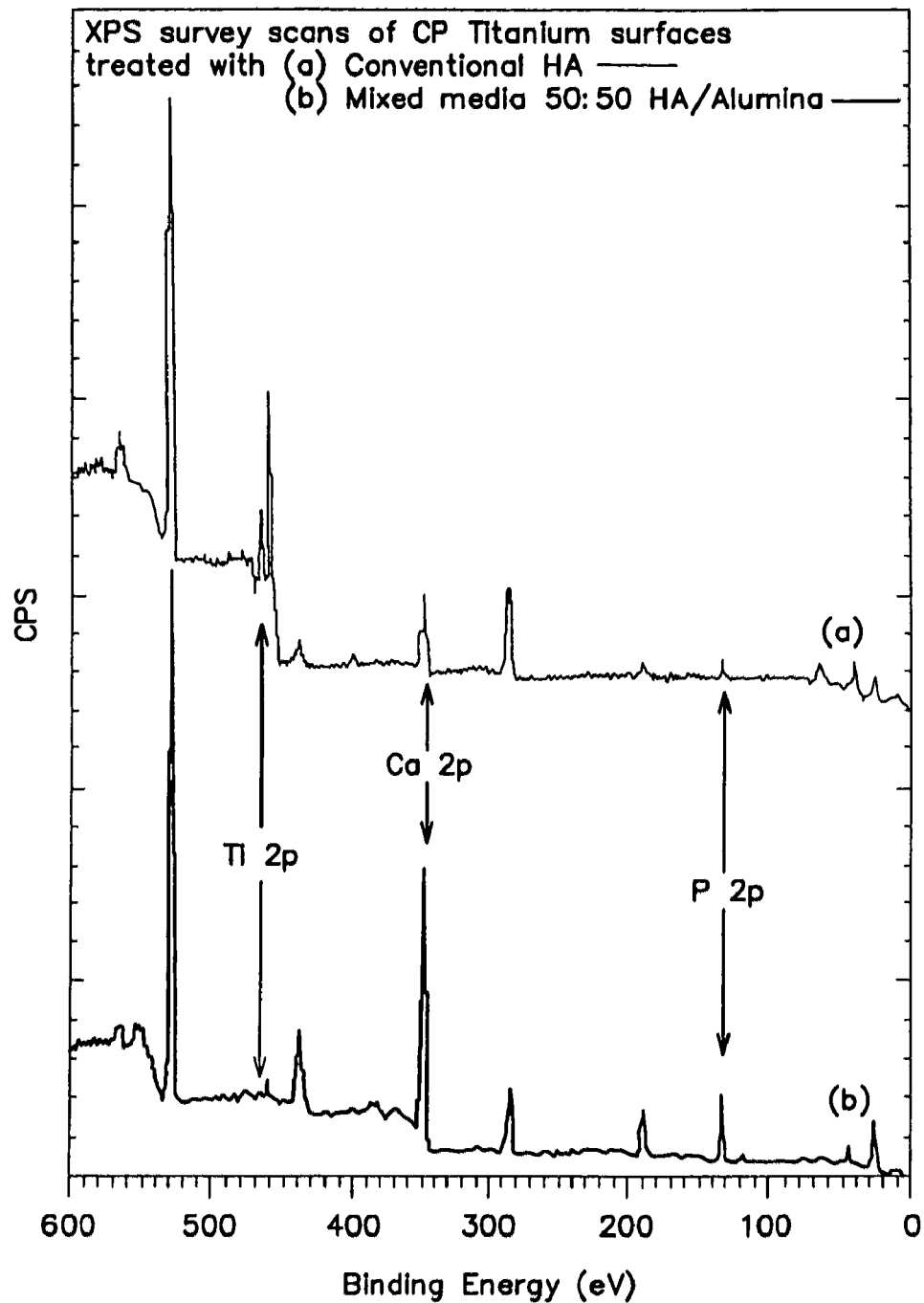
FIG. 2A is an XPS spectrum of cp titanium surfaces grit blasted with HA only.
FIG. 2B is an XPS spectrum of cp titanium surfaces grit blasted with HA:Alumina mix.
Figure 3:
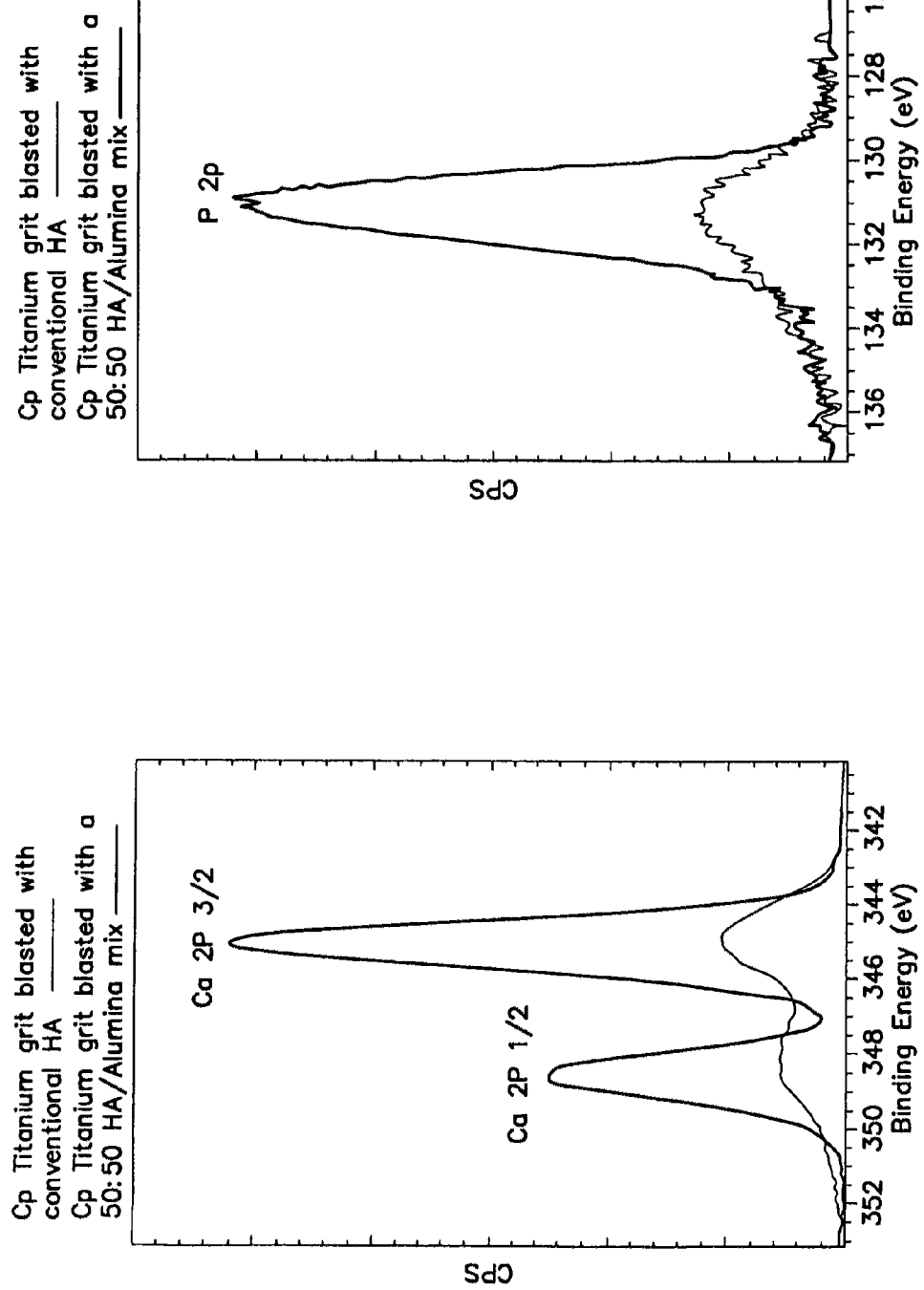
FIGS. 3A and 3B show comparative XPS spectra of Ca 2p (FIG. 3A) and P 2p (FIG. 3B) core levels of HA only blasted cp titanium (fine line) and 50:50 HA:alumina blasted cp titanium (coarse line)
Figure 4:
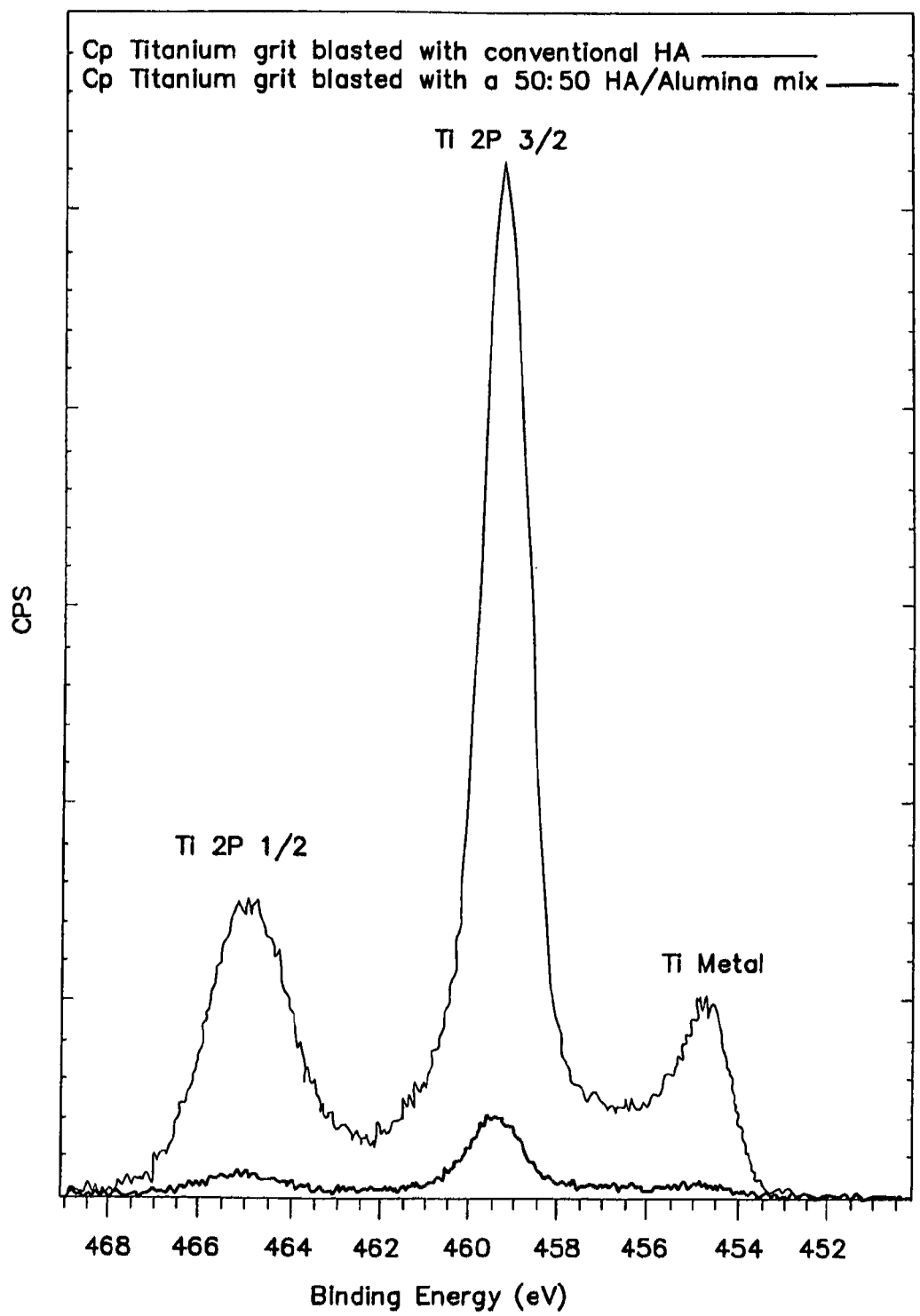
FIG. 4 shows XPS spectra of the Ti 2p core level on the sample grit blasted with 100% HA (top) and the sample grit blasted with a 50:50 HA:alumina mix (bottom)

Samples were submitted for XPS (X-Ray photoelectron spectroscopy) analysis to determine the relative concentration of Ca, P, Ti and Al at the surfaces. FIG. 2 shows the wide scans of both samples, where FIG. 2A is an XPS survey scan of titanium treated with hydroxyapatite, and FIG. 2B is an XPS survey scan of titanium treated with the mixed media of 50:50 HA/alumina. As can be seen the concentration of Ca and P (indicative of HA) in the sample grit blasted using the mixed media technique was significantly higher than those seen in the sample grit blasted with HA only. This is further confirmed by the higher resolution scans of the narrow regions. FIGS. 3 and 4 show the Ca 2p, P 2p and Ti 2p core levels on the 50% HA: 50% Alumina and 100% HA samples. Specifically, FIGS. 3A and 3B show comparative XPS spectra of Ca 2p (FIG. 3A) and P 2p (FIG. 3B) core levels of HA only blasted cp titanium (fine line) and 50:50 HA:alumina blasted cp titanium (coarse line), and FIG. 4 shows XPS spectra of the Ti 2p core level on the sample grit blasted with 100% HA (top) and the sample grit blasted with a 50:50 HA:alumina mix (bottom), indicating that the titanium is substantially covered by HA. In the case of the mixed media grit blasted sample a significant increase in the concentration of both Calcium and Phosphorous was observed in comparison with the sample blasted with HA only. Furthermore the Ca:P ratio was found to be 1.65 confirming that the material on the surface was indeed HA.

A further indication of the presence of a significant surface layer of HA was the greatly reduced Ti concentration observed at the mixed media blasted surface in comparison with that observed at the 100% HA blasted surface indicating a layer of HA of substantial thickness (>10 nm). XPS can be used to calculate the relative concentrations of species at a surface to within an error of 10%) by normalizing the areas under the core level curves with the RSF (Relative Scattering Factor) for each element. The calculated atomic ratio of Ca/Ti at the surface is given in table 1. This value best represents the level of coverage at the surfaces. In the case of the Alumina/HA grit blasted sample the relative concentration of Ca to Ti is approximately 30 times that observed on the 100% HA blasted sample.

TABLE 1

The atomic ratio of Ca/Ti as determined from the narrow XPS scans at the surface of the grit blasted Cp Ti surfaces

| BLASTING MEDIA (WEIGHT %/WEIGHT %) | CA/TI RATIO | RELATIVE RATIO |
|---|---|---|
| 100% HA | 0.45 | 0.98 |
| 100% HA | 0.47 | 1.02 |
| 50% HA:50% Alumina | 13.43 | 29.20 |
| 50% HA:50% Silica bead | 1.96 | 4.26 |
| 50% HA:50% Silica bead | 2.01 | 4.37 |

Figure 5:
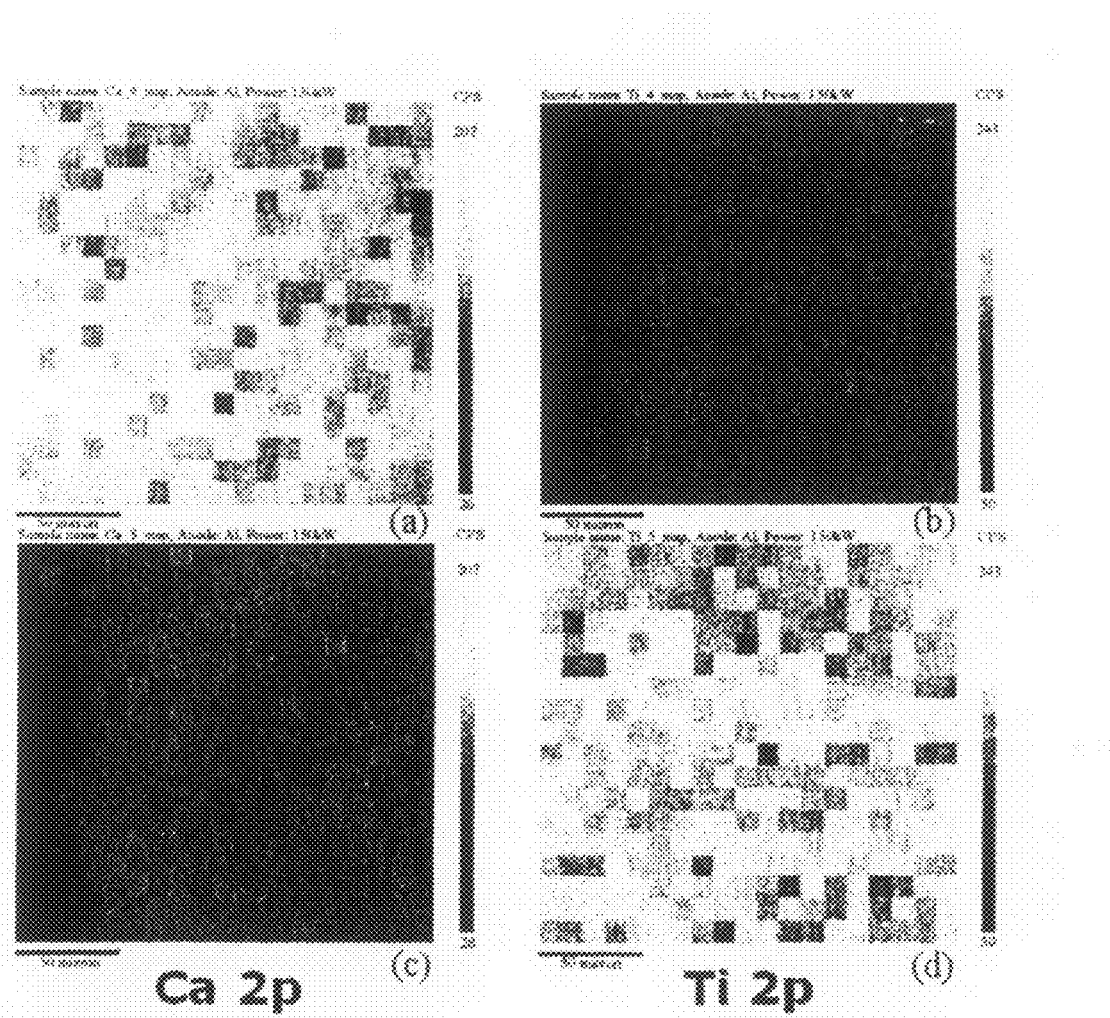
FIG. 5 shows XPS maps of a 0.2×0.2 mm square on cp titanium surfaces showing (a) concentration and distribution of Ca on 50:50 grit blasted sample, (b) concentration and distribution of Ti on 50:50 grit blasted sample; (c) concentration and distribution of Ca on the 100% HA grit blasted sample; (d) concentration and distribution of Ti on the 100% HA grit blasted sample.

In order to assess the uniformity of the HA concentration coating on the surface XPS surface maps (0.2×0.2 mm) were run on both samples sitting on the Ti 2P and Ca 2P peaks, the right and left panels of FIG. 5 respectively. The uniformity of color observed is indicative of the uniformity of distribution of the HA on the substrate material.

These results indicate that simultaneous bombardment allows the HA to become impregnated in the titanium surface. Further more given that both samples were subjected to a rigorous ultrasonic cleaning cycle, it is likely that the HA that remains on the surface was strongly bound on the substrate.

Example 2

This Example describes the modification of a titanium substrate using hydroxyapatite as the dopant and silica bead as the abrasive.

A mixed media was prepared consisting of 50 weight percent silica bead (Honite 14: 75-150 micron particle size range, Mohs hardness 5 Guyson international Ltd) and 50 weight percent HA (Fluka Synthetic hydroxyapatite). A Rocatec™ grit blaster operating at a pressure of 5 bar was used to grit blast two 2 cm×2 cm CP Titanium coupon (Titanium Sheet Grade 2 Medical to ASTM F67 Spec). The nozzle to surface distance was 1 cm and the nozzle was held at 90° to the surface. The silicon carbide nozzle had an orifice diameter of 1 mm and traversed the surface at 2 cm sec$^{-1}$. The surface was subjected to three passes.

The samples were then subjected to a cleaning treatment involving 20 minutes ultrasonic washing in deionized water to remove any material that was not intimately affixed to the surface. After the ultrasonic cleaning the samples were rinsed with deionized water and air-dried in an oven at 95° C. for one hour.

Figures 6A, 6B:
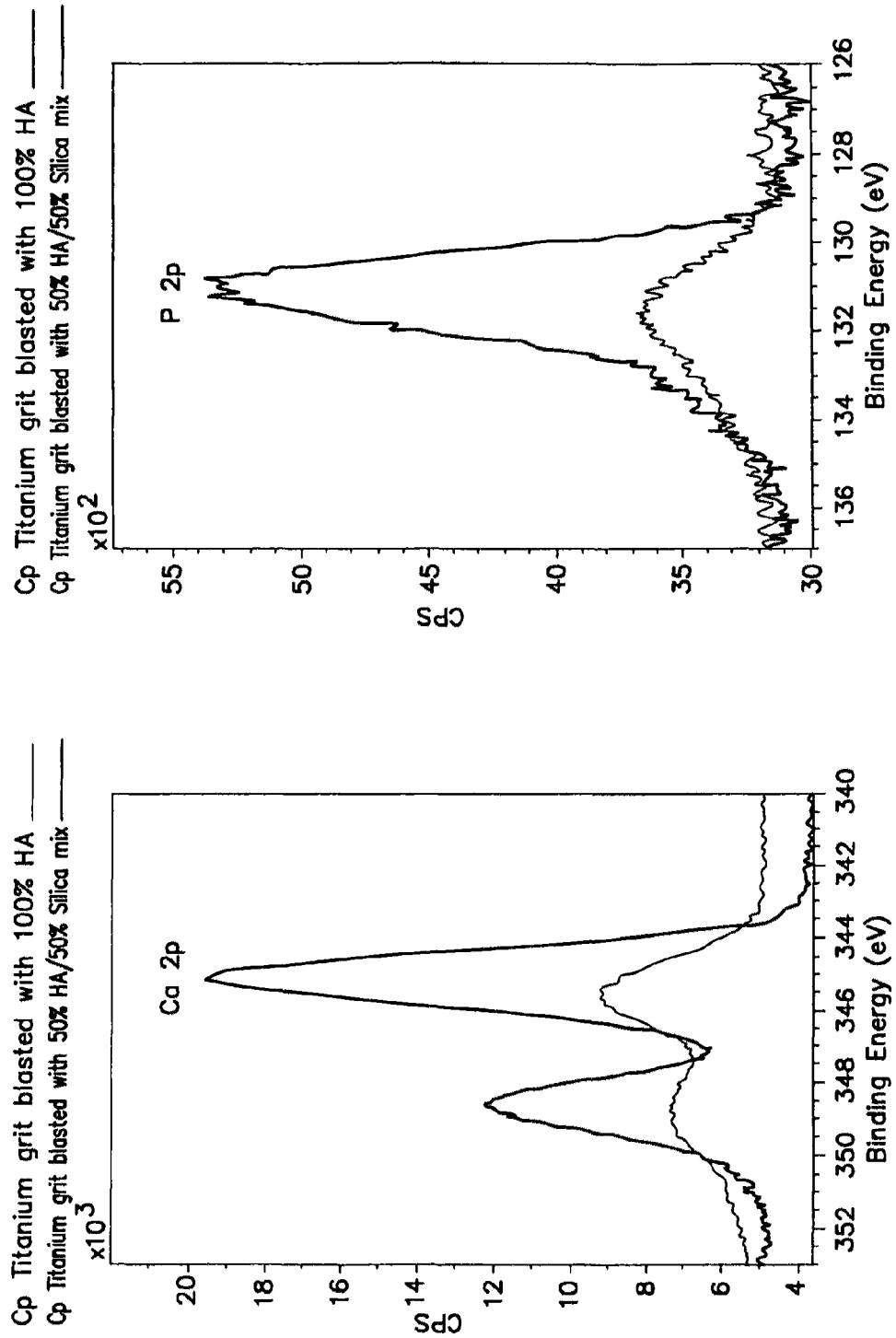
FIGS. 6A and 6B show comparative XPS spectra of the Ca 2p and P 2p core levels in the case of HA only blasted Cp titanium (fine line) and 50:50 HA:silica bead blasted cp titanium (coarse line)

Samples were submitted for XPS (X-Ray photoelectron spectroscopy) analysis to determine the relative concentration of Ca, P, Ti and Si at the surfaces. A comparison of are Ca 2p core level in one of the samples and the 100% HA grit blasted sample is shown in the right panel of FIG. 6. The P 2p core levels on both samples are shown in the left panel of FIG. 6. In the case of the mixed media grit blasted sample a significant increase in the concentration of both calcium and phosphorous was observed in comparison with the sample blasted with HA only although not as high as was the case with alumina.

Figure 7:
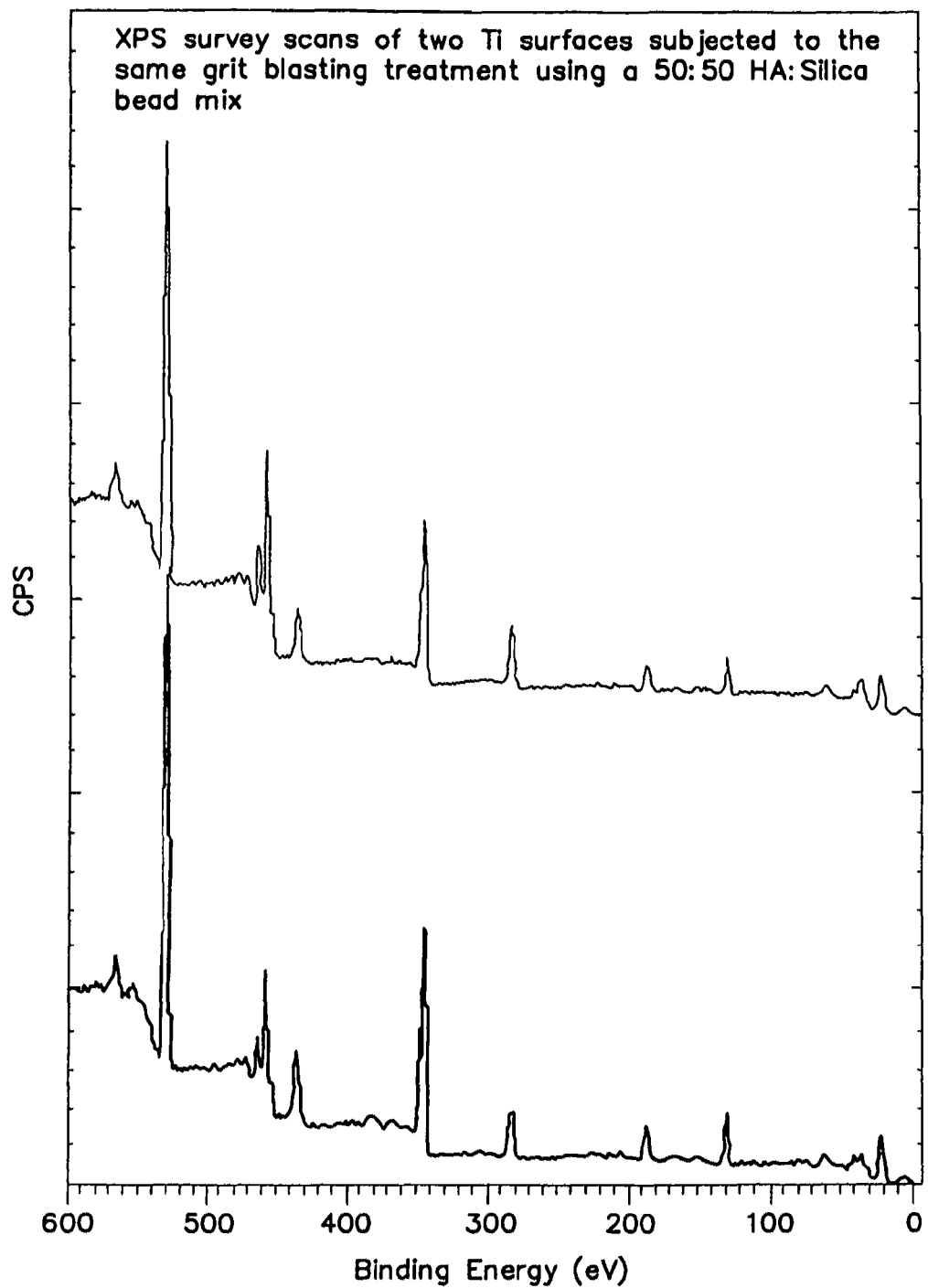
FIG. 7 is a pair of XPS survey scans of two different samples blasted with a 50:50 HA/silica bead mix, showing the reproducibility of the results.

The calculated atomic ratio of Ca/Ti at the surfaces is given in Table 1. In the case of the silica bead/HA grit blasted sample the relative concentration of Ca to Ti is approximately 4 times that observed on the 100% HA blasted samples. Table 1 also demonstrates the reproducibility of the results achievable with this technique given that the Ca/Ti ratio measured on the samples treated with the same mixed media are approximately the same. This is further demonstrated in FIG. 7 which shows the similarity in the survey scans of the two samples.

Example 3

This Example describes the modification of a titanium substrate using hydroxyapatite/gentamycin as the dopant and alumina bead as the abrasive.

A mixed media was prepared consisting of 50 weight percent alumina (White Saftigrit: Mesh size 150, 88 micron particle size, Mohs hardness 9, Guyson international Ltd), 40 weight percent HA (Fluka Synthetic hydroxyapatite) and 10 weight percent Gentamycin. A Rocatec™ grit blaster operating at a pressure of 5 bar was used to grit blast three 0.5 cm×0.5 cm CP titanium coupons (Titanium Sheet Grade 2 Medical to ASTM F67 Spec). Control coupons were blasted with HA and alumina only. The nozzle to surface distance was 1 cm and the nozzle was held at 900 to the surface. The silicon carbide nozzle had an orifice diameter of 1 mm and traversed the surface at 2 cm sec$^{-1}$. The surface was subjected to three passes.

The samples were then subjected to a cleaning treatment involving 20 minutes ultrasonic washing in deionized water to remove any material that was not intimately affixed to the surface. After the ultrasonic cleaning the samples were rinsed with deionized water and air-dried in an oven at 40° C. for one hour.

The release and antibacterial activity of the antibiotic loaded surfaces was evaluated against three bacterial species [*Staphylococcus aureus* (FIG. 8.1), *Escherichia coli* (FIG. 8.2) and *Pseudomonas aeruginosa* (FIG. 8.3)], identified as opportunistic pathogens colonizing peri-prosthetic tissue post operation and a major cause of the corrosion of implants, using an agar disc-diffusion method.

In brief, the bacteria were grown from stock cultures on brain heart infusion (BHI) agar at 37° C. for 16 h and isolated colonies were used to seed fresh cultures in 10 ml Luria Broth (LB). After incubation at 37° C. for 12-16 h with shaking (200 rpm), the cultures were diluted in Mueller Hinton (MH) broth to give an OD 600 of 0.05. A 350-µl volume of each bacterial suspension was streaked using clinical swabs on MH agar plates containing agar to a depth of 4 mm. Following this the coupons of material were placed on the agar. The plates were inverted and incubated under aerobic conditions (36 h, 37° C.).

The possibility that the implant material was inhibitory with respect to microbial growth independent of the activity of the released Gentamycin was eliminated by using the control samples not having the antibiotic loaded on the surface (negative control) labeled 1 in FIGS. 8.1, 8.2, and 8.3 respectively. The antibiotic loaded samples are labeled 2 in FIGS. 8.1, 8.2, and 8.3 respectively.

The results are shown in FIG. 8. In the case of each of the three bacterial species tested, an inhibition zone where bacterial growth is inhibited (labeled IZ in FIGS. 8.1, 8.2 and 8.3 respectively) was seen around the HA/Gentamycin treated samples. This indicates that the Gentamycin was incorporated into the surface by the process and furthermore that the antibiotic remains active through the blasting process.

Example 4

This Example describes the modification of a titanium substrate using hydroxyapatite/vancomycin as the dopant and alumina bead as the abrasive.

A mixed media was prepared consisting of 67 weight percent alumina (White Saftigrit: Mesh size 150, 88 micron particle size, Mohs hardness 9, Guyson international Ltd), 30 weight percent HA (Fluka Synthetic hydroxyapatite) and 3 weight percent Vancomycin. A Rocatec™ grit blaster operating at a pressure of 5 bar was used to grit blast eighteen 10 mm diameter Grade 5 titanium discs (Titanium 6AL-4V Sheet Medical to ASTM F136 Spec). Control discs were blasted with HA and alumina only. The nozzle to surface distance was 0.5 cm and the nozzle was held at 90° to the surface. The silicon carbide nozzle had an orifice diameter of 1 mm and traversed the surface at 2 cm sec-1. The surface was subjected to three passes.

A number of the samples were then subjected to a cleaning treatment involving 20 minutes ultrasonic washing in deionized water to remove any material that was not intimately affixed to the surface. After the ultrasonic cleaning the samples were rinsed with deionized water and allowed to air-dry in an oven at 40° C. for one hour.

Figure 10:
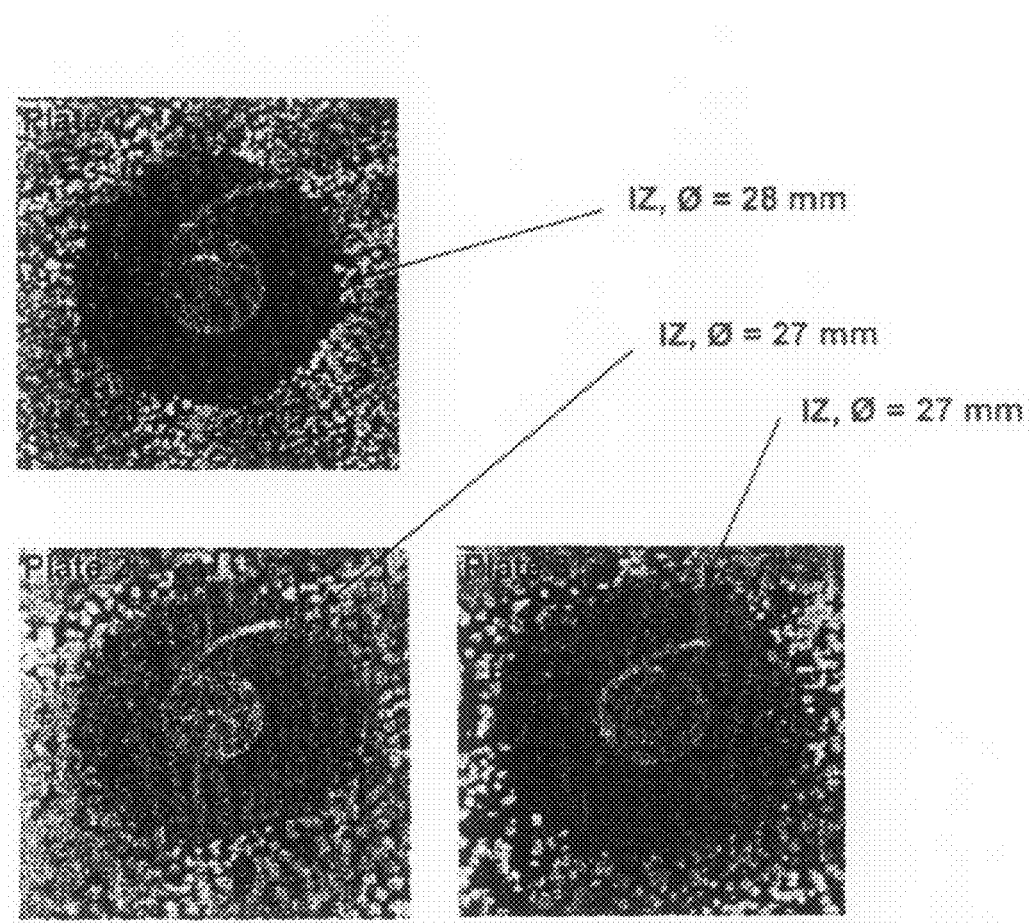
FIG. 10, shows three photographs of the inhibition zone (IZ) on an agar plate inoculated with *S. aureus* and exposed to vancomycin coupon (Plate 1) and inoculated with *E. Coli* and exposed to Tobramycin (Plates 2 and 3)

The release and antibacterial activity of the antibiotic loaded surfaces was evaluated against the bacterial species *Staphylococcus aureus* (NCIMB 9518), identified as an opportunistic pathogen colonizing peri-prosthetic tissue post operation, using an agar disc-diffusion method. FIG. 10, Plate 1 is a photograph of the inhibition zone (IZ) on an agar plate inoculated with *S. aureus* and exposed to the vancomycin-doped coupon.

Tests were carried out according to BSAC (British Society for Antimicrobial Chemotherapy) Disc Diffusion method for Antimicrobial Susceptibility testing (Version 2.1.1, January 2002). A bacterial suspension containing $10^7$ CFU/ml of *Staphylococcus aureus* NCIMB 9518 was prepared from fresh overnight cultures, and 0.5 ml of this suspension was homogeneously spread onto isosensitest agar plates. Following this the coupons of material were placed on the agar. The plates were incubated under aerobic conditions (20 hours @ 37° C.).

The possibility that the implant material was inhibitory with respect to microbial growth was eliminated by using control samples not having the antibiotic loaded on the surface (negative control).

The results are shown in FIG. 10 plate 1, as demonstrated by an inhibition zone pointing to inhibited bacterial growth around the HA/vancomycin treated samples. This indicates that the vancomycin was incorporated into the surface by the process and furthermore that the antibiotic remains active through the blasting process.

Example 5

This Example describes the modification of a titanium substrate using hydroxyapatite/tobramycin as the dopant and alumina bead as the abrasive.

A mixed media was prepared consisting of 67 weight percent alumina (White Saftigrit: Mesh size 150, 88 micron particle size, Mohs hardness 9, Guyson international Ltd), 30 weight percent HA (Fluka Synthetic hydroxyapatite) and 3 weight percent Tobramycin. A Rocatec™ grit blaster operating at a pressure of 5 bar was used to grit blast eighteen 10 mm diameter Grade 5 titanium discs (Titanium 6AL-4V Sheet Medical to ASTM F136 Spec). Control discs were blasted with HA and alumina only. The nozzle to surface distance was 0.5 cm and the nozzle was held at 90° to the surface. The silicon carbide nozzle had an orifice diameter of 1 mm and traversed the surface at 2 cm sec-1. The surface was subjected to three passes.

A number of the samples were then subjected to a cleaning treatment involving 20 minutes ultrasonic washing in deionized water to remove any material that was not intimately affixed to the surface. After the ultrasonic cleaning the samples were rinsed with deionized water and allowed to air-dry in an oven at 40° C. for one hour.

The release and antibacterial activity of the antibiotic loaded surfaces was evaluated against the bacterial species *Escherichia coli* (NCIMB 12210), identified as an opportunistic pathogen colonizing peri-prosthetic tissue post operation, using an agar disc-diffusion method. FIG. 10, Plates 2 and 3 are photographs of the inhibition zone (IZ) on an agar plate inoculated with *E. Coli* and exposed to the tobramycin doped coupon.

Tests were carried out according to BSAC (British Society for Antimicrobial Chemotherapy) Disc Diffusion method for Antimicrobial Susceptibility testing (Version 2.1.1, January 2002). A bacterial suspension containing $10^7$ CFU/ml of *E. coli* NCIMB 12210 was prepared from fresh overnight cultures, and 0.5 ml of this suspension was homogeneously spread onto isosensitest agar plates. Following this the coupons of material were placed on the agar. The plates were incubated under aerobic conditions (20 hours @ 37° C.).

The possibility that the implant material was inhibitory with respect to microbial growth was eliminated by using control samples not having the antibiotic loaded on the surface (negative control).

The results are shown in FIG. 10, Plates 2 and 3, as demonstrated by an inhibition zone pointing to inhibited bacterial growth around the HA/Tobramycin treated samples. This indicates that the Tobramycin was incorporated into the surface by the process and furthermore that the antibiotic remains active through the blasting process.

Example 6

This example describes the modification of a titanium substrate using hydroxyapatite as the dopant and abrasives of varying size/hardness.

A mixed media was prepared consisting of 80 weight percent abrasive (50, 100 micron particle size Silica bead, Mohs hardness 6, Comco Inc.; 50, 100, 150 micron particle size Alumina bead, Mohs hardness 9, Comco Inc.) and 20 weight percent HA (Fluka Synthetic hydroxyapatite). A Comco MB1000 Micro-blaster operating at a blast pressure of 80 psi was used to grit blast nine 10 mm diameter Grade 5 titanium discs (Titanium 6AL-4V Sheet Medical to ASTM F136 Spec) for each abrasive type. The nozzle to surface distance was 15 mm and the nozzle was held at 90° to the surface. The HP (high performance) nozzle used had an orifice diameter of 0.060 inch and traversed the surface at 3.175 mmsec-1. The surface was subjected to one pass through the centre of each metal disc.

The samples were then subjected to a cleaning treatment involving 20 minutes ultrasonic washing in deionized water to remove any material that was not intimately affixed to the surface. After the ultrasonic cleaning the samples were rinsed with deionized water and air-dried in an oven at 40° C. for one hour.

Samples were submitted for XPS (X-Ray photoelectron spectroscopy); FTIR (Fourier Transform Infrared Spectroscopy); Surface Roughness analysis-Stylus Profilometry; (XRD) X-Ray Diffraction, to determine the relative concentration of Ca, P, and Ti at the surface of each sample in conjunction with the morphological characteristics of each sample.

Figure 11A:
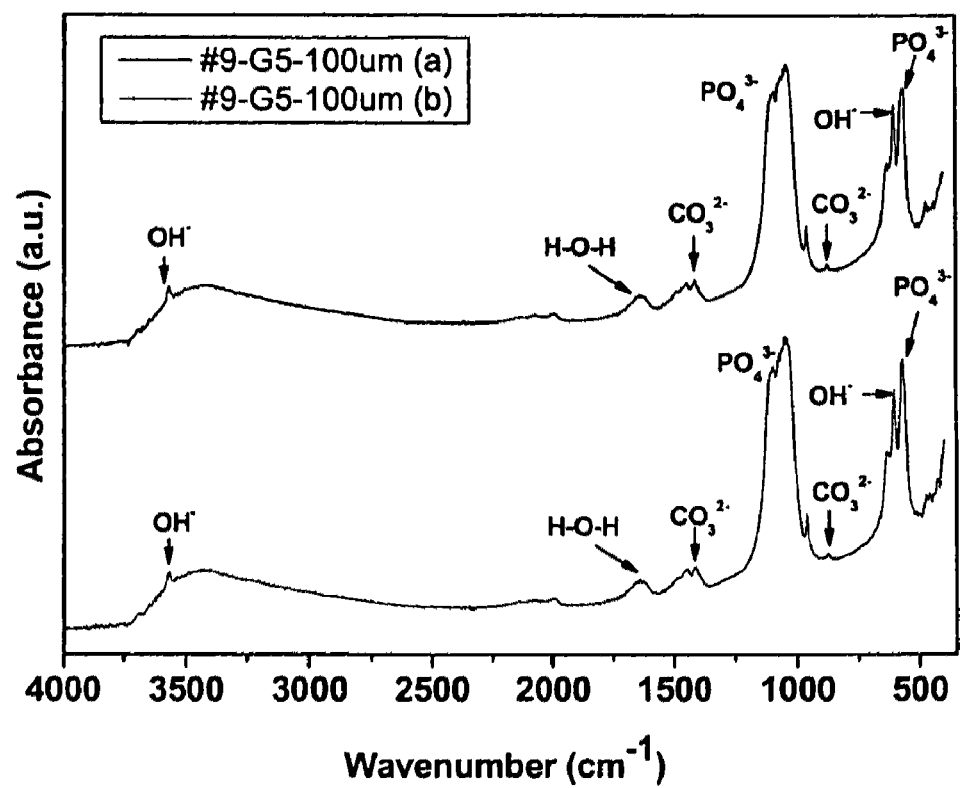
FIG. 11A shows FTIR spectra of duplicate 100 μm alumina bead samples (a) and (b)
Figure 11B:
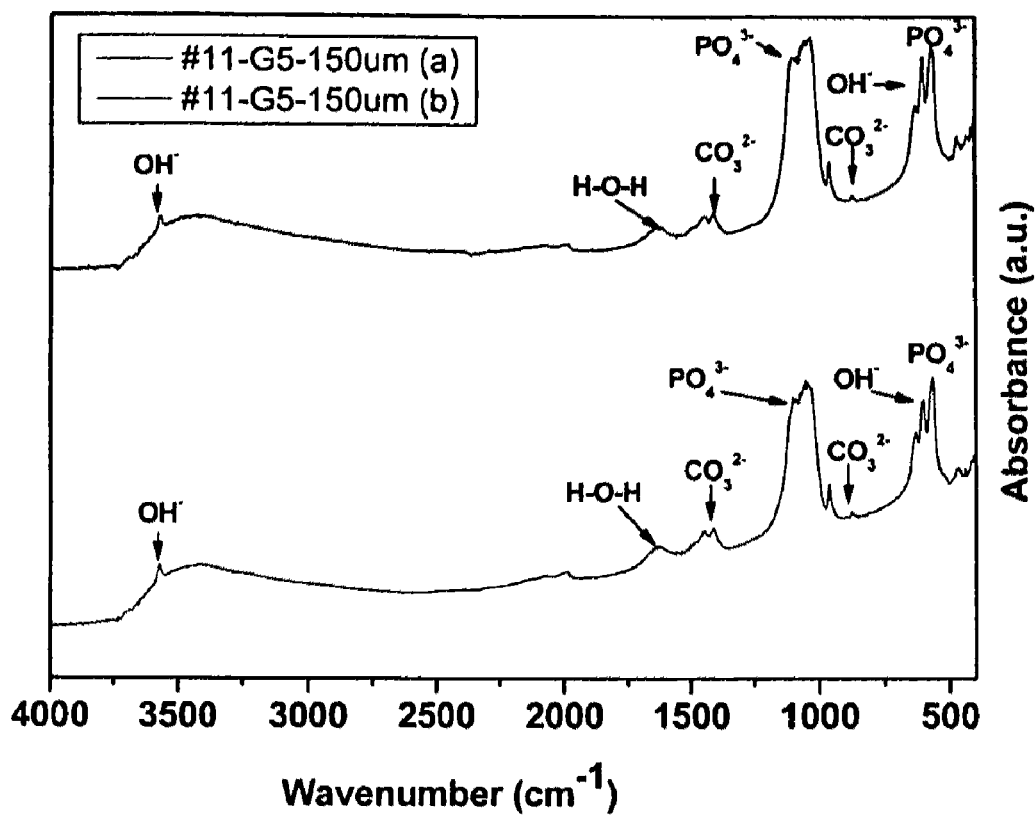
FIG. 11B shows FTIR spectra of duplicate 150 μm alumina bead samples (a) and (b)

Table 2 indicates the results shown for titanium blasted with abrasives of varying particle size and hardness, as indicated by XPS. FIGS. 11A and 11B show FTIR spectra plots for duplicate 100 μm and 150 μm alumina bead respectively.

TABLE 2

XPS atomic concentrations of surface elements (and Ca:P ratio) as a function of blast particle size and hardness

| Elements | Control | 100 μM Glass Bead | 50 μM Alu Oxide Bead | 100 μM Alu Oxide Bead | 150 μM Alu Oxide Bead |
|---|---|---|---|---|---|
| O 1s | 37.78 | 54.80 | 53.38 | 54.71 | 54.12 |
| C 1s* | 44.33 | 20.73 | 24.95 | 23.08 | 24.02 |
| N 1s | 3.37 | 0.25 | 0.57 | 0.84 | 0.55 |
| Ti 2p | 5.00 | 0.23 | 1.18 | 1.32 | 0.86 |
| Ca 2p | 0.28** | 14.58 | 12.23 | 12.36 | 11.99 |
| P 2p | 0.29** | 9.40 | 7.69 | 7.68 | 8.47 |
| Al 2p | 8.94*** | — | — | — | — |
| Ca/P Ratio | n/a | 1.55 | 1.61 | 1.61 | 1.42 |

*Normal adventitious Carbon level on Titanium & its alloys - can be higher depending on the forming/manufacturing processes undergone.

**Adventitious HA due to cross contamination from treated samples.

***Aluminium in the TiAl$_4$V$_6$ alloy (Grade 5 Titanium).

FIG. 11A shows FTIR spectra of duplicate 100 μm alumina bead samples (a) and (b), and FIG. 11B shows FTIR spectra of 150 duplicate μm alumina bead samples (a) and (b).

Table 3 indicates the results shown for abrasives of varying particle size and hardness, as indicated by stylus profilometry.

TABLE 3

Stylus profilometry of surface topography showing roughness as a function of blast particle size and hardness

|  | 100 μM Glass Bead | 50 μM Alu Oxide Bead | 100 μM Alu Oxide Bead | 150 μM Alu Oxide Bead |
|---|---|---|---|---|
| Avg. Surface Roughness (μM) | 0.35 | 0.37 | 0.62 | 0.61 |
| Std Dev | 0.06 | 0.03 | 0.05 | 0.02 |

Figure 12A:
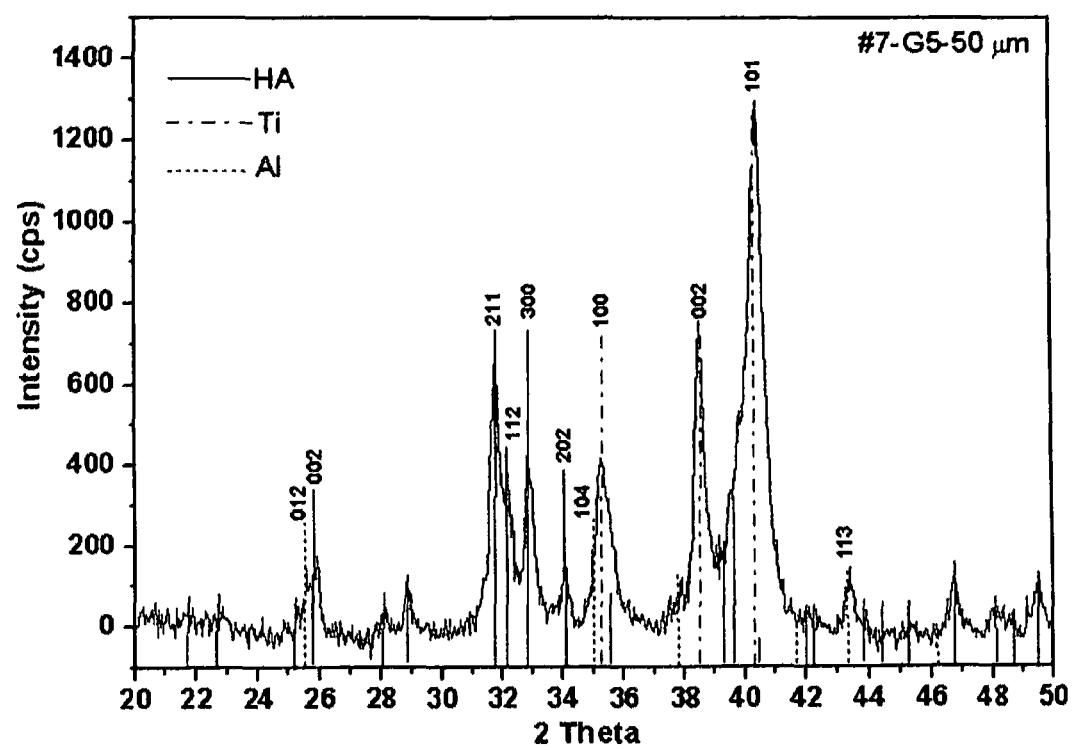
FIG. 12A is an XRD pattern of surface HA (alumina; 50 μm)
Figure 12B:
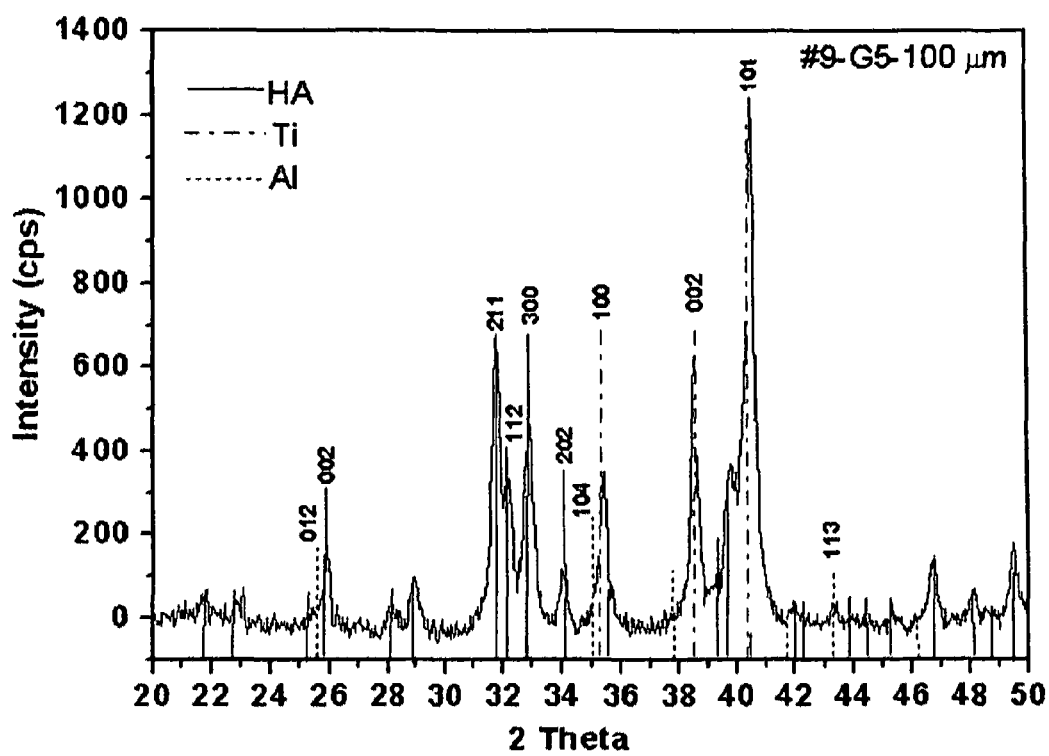
FIG. 12 B is an XRD pattern of surface HA (alumina; 100 μm)

FIGS. 12A and 12B show XRD patterns for 50 μm and 100 μm alumina bead samples, respectively.

The data indicates that varying the size and hardness of the abrading media will result in varying surface morphology as expected, but also in differences in the quantity and coverage of Hydroxyapatite in the adlayer.

Example 7

This Example describes the modification of a titanium substrate by delivering hydroxyapatite as the dopant in one particle stream and alumina bead as the abrasive in a separate particle stream using a twin nozzle, while varying blast parameters and the abrasive to dopant ratio.

An experiment was conducted to control the uniformity of the flow of abrasive and dopant materials to the surface being treated by loading the materials into the reservoirs of two separate Comco MB 1000 Micro-blaster units feeding separate nozzles aimed at the same point on the surface, as schematically depicted in FIG. 9C. The following parameters were varied; nozzle diameters, distance of nozzles from the surface, blast pressure, incident angle and the ratio of abrasive to dopant at the point of contact with the substrate (See Table 4: Test Parameters variations to study effect on HA deposition and surface topography). 100 micron particle size Alumina bead, (Mohs hardness 9, Comco Inc.) was used in all test runs. The Synthetic HA (Glantreo Ltd, Cork, Ireland) used had a particle size range of 20 to 60 microns. Nine 10 mm diameter Grade 5 titanium discs (Titanium 6AL-4V Sheet Medical to ASTM F136 Spec) were treated for each run. The surface was subjected to one pass through the centre of each metal disc at a feed rate of 3.175 mmsec-1.

TABLE 4

Test Parameter variations to study effect on HA deposition and surface topography

| Run | A: Nozzle Diameter | B: Nozzle Distance | C: Blast Pressure | D: Incident Angle | E: Abrasive to Dopant Ratio |
|---|---|---|---|---|---|
| 1 | 30 | 12 | 95 | 90 | 70:30 |
| 2 | 30 | 18 | 95 | 45 | 90:10 |
| 3 | 60 | 18 | 60 | 90 | 90:10 |
| 4 | 30 | 18 | 95 | 90 | 90:10 |
| 5 | 46 | 15 | 80 | 67.5 | 80:20 |
| 6 | 30 | 12 | 95 | 45 | 70:30 |
| 7 | 60 | 12 | 60 | 90 | 70:30 |
| 8 | 30 | 12 | 60 | 45 | 90:10 |
| 9 | 30 | 18 | 60 | 90 | 70:30 |
| 10 | 60 | 18 | 95 | 45 | 70:30 |
| 11 | 60 | 12 | 60 | 45 | 70:30 |
| 12 | 60 | 18 | 60 | 45 | 90:10 |
| 13 | 30 | 12 | 60 | 90 | 90:10 |
| 14 | 60 | 12 | 95 | 90 | 90:10 |
| 15 | 60 | 12 | 95 | 45 | 90:10 |
| 16 | 30 | 18 | 60 | 45 | 70:30 |
| 17 | 60 | 18 | 95 | 90 | 70:30 |

The samples were then subjected to a cleaning treatment involving 20 minutes ultrasonic washing in deionized water to remove any material that was not intimately affixed to the surface. After the ultrasonic cleaning the samples were rinsed with deionized water and air-dried in an oven at 40° C. for one hour.

Samples were submitted for XPS (X-Ray photoelectron spectroscopy); FTIR (Fourier Transform Infrared Spectroscopy); Surface Roughness analysis-Stylus Profilometry; to determine the relative concentration of Ca, P, and Ti at the surface of each sample in conjunction with the morphological characteristics of each sample. Results for XPS analysis are shown in Table 5 and results for stylus profilometry are shown in Table 6.

TABLE 5

XPS atomic concentrations of surface elements (and CA:P ratio) as a function of varying blast parameters and abrasive to dopant ratio.

| Element | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| O 1s | 45.7 | 48.7 | 49.3 | 43.9 | 44.8 | 44.6 | 51.1 | 39.8 | 48.0 | 42.9 | 51.0 | 50.0 | 50.8 | 46.2 | 48.8 | 47.8 | 53.2 |
| C 1s* | 32.6 | 32.9 | 32.6 | 36.2 | 34.2 | 42.7 | 30.1 | 44.7 | 30.4 | 40.3 | 36.5 | 34.2 | 27.1 | 37.3 | 31.3 | 31.0 | 30.1 |
| Na 1s | 0.6 | 0.3 | 0.0 | 0.4 | 0.3 | 1.1 | 1.9 | 0.7 | 0.2 | 0.7 | 1.9 | 1.8 | 0.4 | 3.6 | 1.3 | 0.4 | 2.1 |
| Ti 2p | 0.4 | 2.9 | 2.0 | 2.0 | 1.8 | 5.7 | 3.7 | 6.7 | 0.2 | 3.3 | 6.0 | 5.2 | 0.7 | 2.8 | 3.7 | 0.7 | 4.7 |
| Ca 2p | 13.3 | 10.1 | 10.3 | 11.2 | 12.3 | 4.0 | 8.2 | 5.6 | 13.5 | 7.9 | 3.1 | 5.7 | 13.9 | 6.8 | 9.3 | 12.9 | 6.4 |
| P 2p | 7.4 | 5.0 | 5.8 | 6.2 | 6.5 | 1.9 | 4.4 | 2.6 | 7.8 | 4.9 | 1.4 | 3.1 | 7.1 | 3.3 | 5.5 | 7.2 | 3.5 |
| Ca/P Ratio | 1.81 | 2.00 | 1.77 | 1.80 | 1.89 | 2.01 | 1.99 | 2.17 | 1.73 | 1.61 | 2.3 | 1.83 | 1.94 | 2.04 | 1.72 | 1.80 | 1.84 |

*Normal adventitious Carbon level on Titanium & its alloys - can be higher depending on the forming/manufacturing processes undergone.

TABLE 6

XPS atomic concentrations of duplicate HA controls

| HA powder control | | Atomic Concentration (%) | |
|---|---|---|---|
| Peak | Position BE (eV) | Point A | Point B |
| O 1s | 532.5 | 38.02 | 40.29 |
| Ca 2p | 346.5 | 13.08 | 13.72 |
| C 1s | 285 | 41.58 | 38.65 |
| P 2p | 133.5 | 7.31 | 7.34 |
| Ca:P ratio | | 1.79 | 1.87 |

TABLE 7

Stylus profilometry of surface roughness as a function of varying blast parameters and abrasive to dopant ratio

| | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| Average Surface Roughness (μM) | 0.50 | 0.46 | 0.59 | 0.40 | 0.55 | 0.41 | 0.51 | 0.46 | 0.43 | 0.57 | 0.53 | 0.55 | 0.51 | 0.53 | 0.55 | 0.48 | 0.54 |
| Std Dev | 0.02 | 0.03 | 0.05 | 0.03 | 0.02 | 0.03 | 0.03 | 0.02 | 0.03 | 0.04 | 0.01 | 0.04 | 0.03 | 0.02 | 0.05 | 0.04 | 0.04 |

Figure 13:
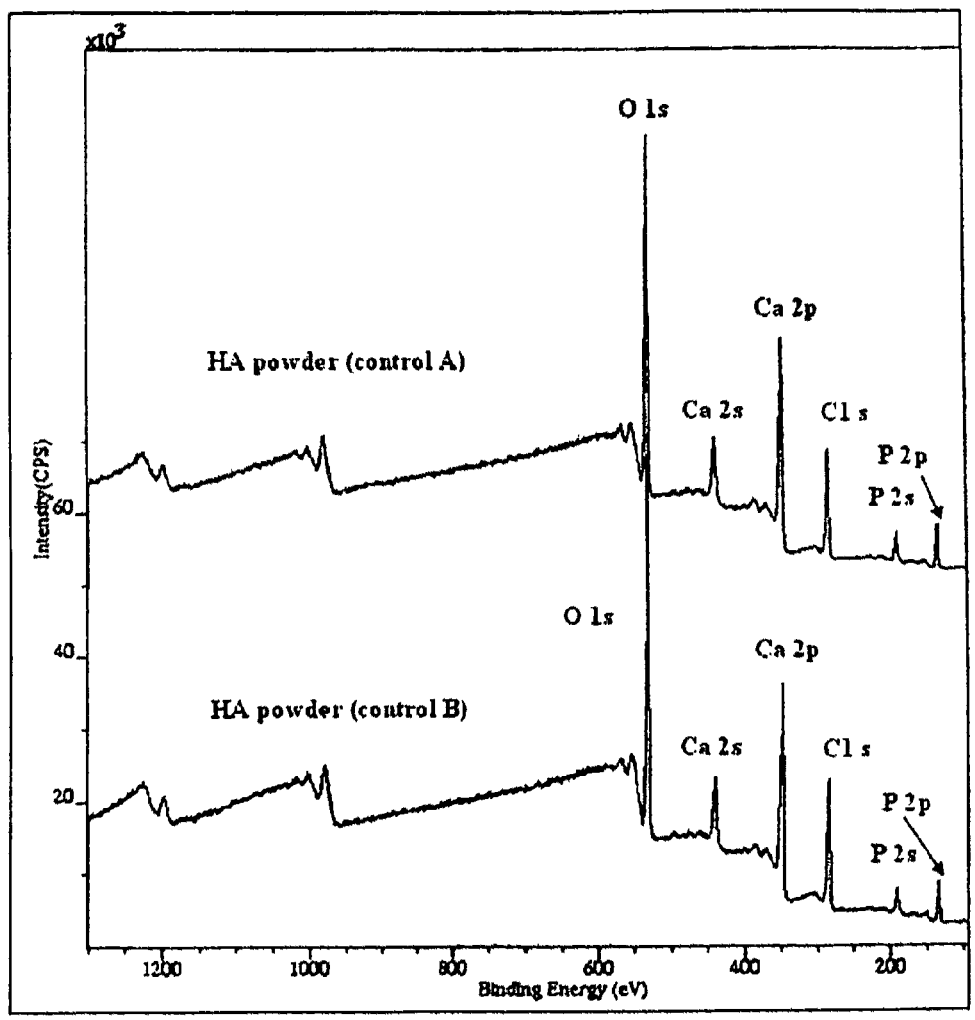
FIG. 13 show XPS survey spectra for duplicate HA controls.

The data indicates that varying the blasting parameters and abrasive:dopant ratio, as outlined in the experiment, results in varying surface morphology as expected, but also in differences in the quantity and coverage of hydroxyapatite in the adlayer. The HA controls data indicates that the process does not have a detrimental effect on the HA quality as exemplified by the Ca:P (calcium to phosphate) ratio data, as shown in FIG. 13, XPS Survey Spectra for duplicate HA controls.

Example 8

This Example describes the modification of a stainless steel substrate and a Grade 2 titanium substrate using hydroxyapatite as the dopant and alumina bead as the abrasive.

A mixed media was prepared consisting of 80 weight percent alumina (White Saftigrit: Mesh size 150, 88 micron particle size, Mohs hardness 9, Guyson international Ltd) and 20 weight percent HA (Synthetic HA, particle size 20-60 microns, Glantreo Ltd, Cork, Ireland). A Rocatec™ grit blaster operating at a pressure of 5 bar was used to grit blast a Stainless Steel tube (Medical grade Stainless Steel to ASTM 1586 spec) used to manufacture cardiac stents) and Grade 2 Titanium sheet (Titanium Sheet Grade 2 Medical to ASTM F67 Spec). The nozzle to surface distance was 0.5 cm and the nozzle was held at 90° to the surface. The silicon carbide nozzle had an orifice diameter of 1 mm and traversed the surface at 2 cm sec-1. The surface was subjected to three passes.

The sample was then subjected to a cleaning treatment involving 20 minutes ultrasonic washing in deionized water to remove any material that was not intimately affixed to the surface. After the ultrasonic cleaning the samples were rinsed with deionized water and air-dried in an oven at 40° C. for one hour.

Figure 14:
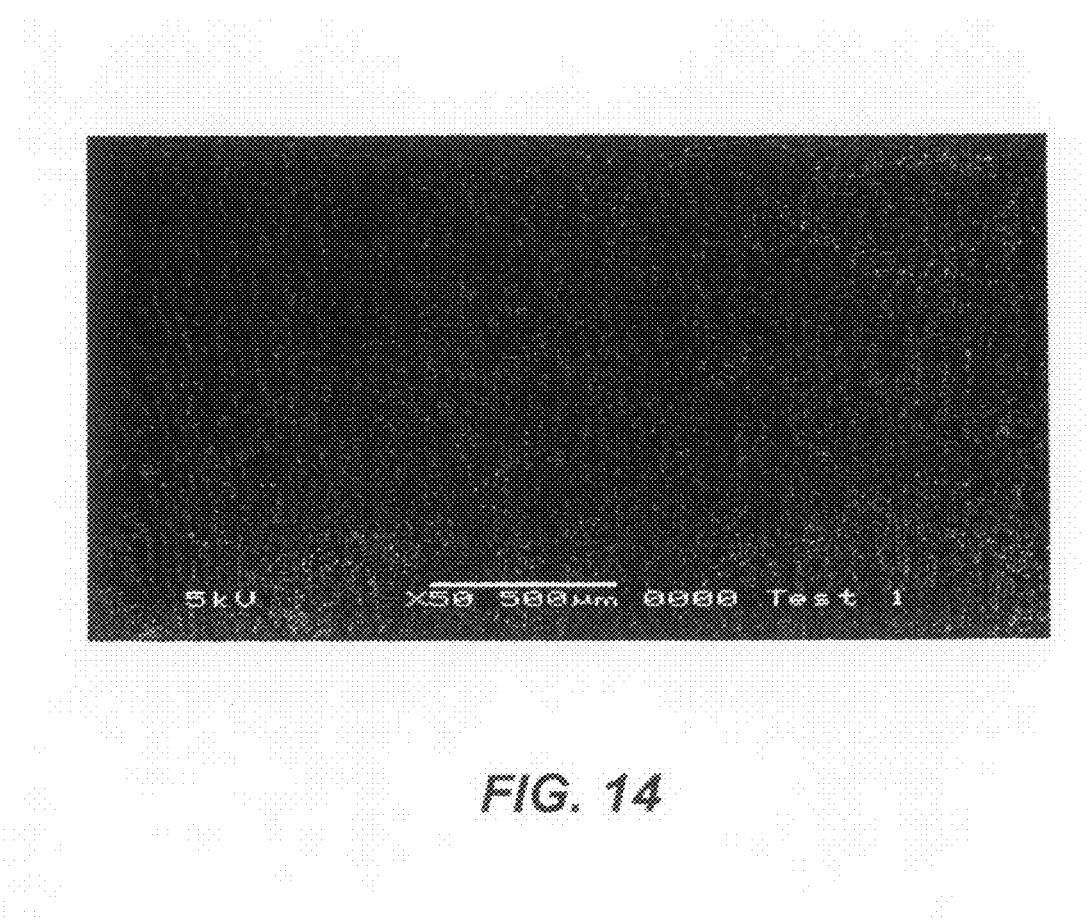
FIG. 14 is an SEM (scanning electron microscopy) image of an HA adlayer on a stainless steel (ASTM F1586) surface.
Figure 15:
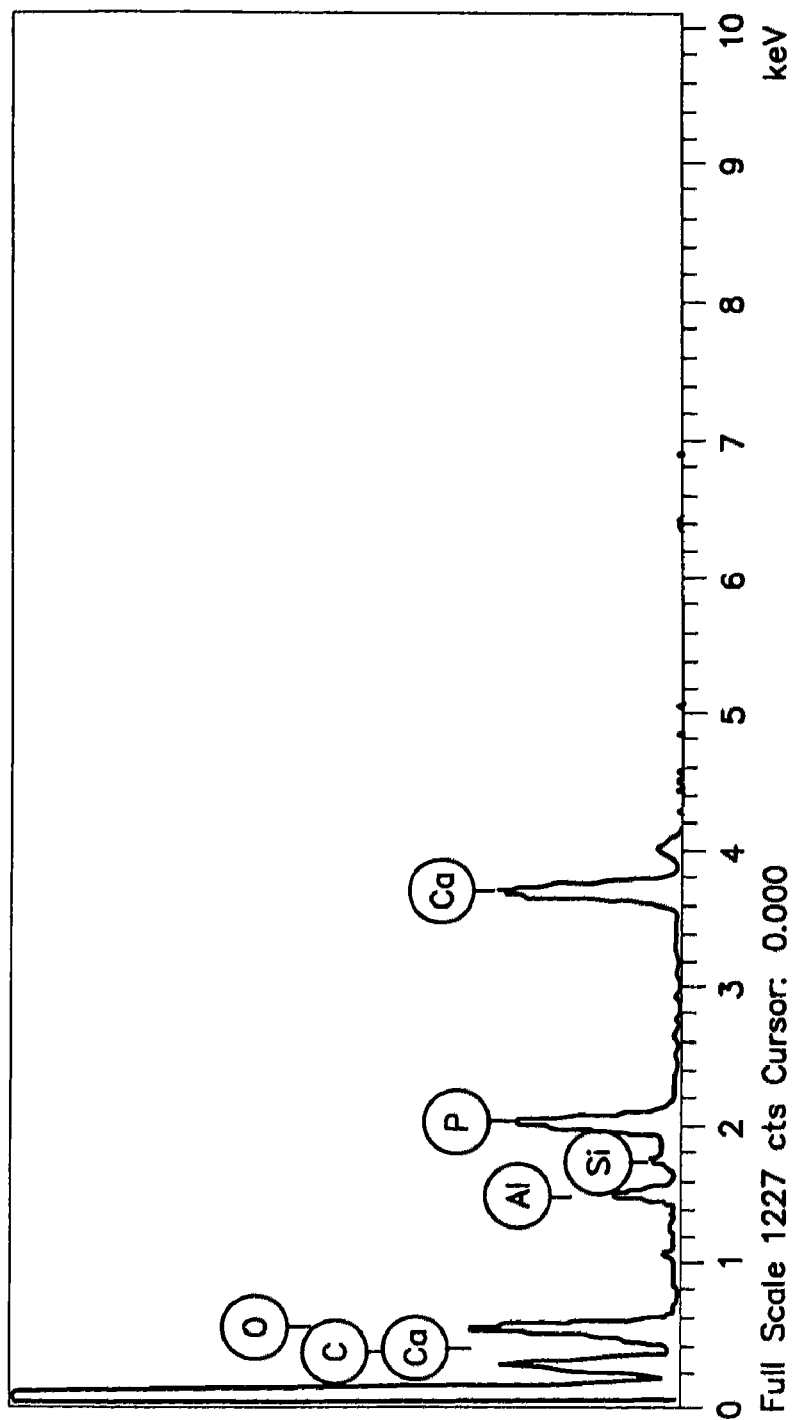
FIG. 15 is an energy dispersive x-ray (EDX) spectrum for HA on a stainless steel (ASTM F1586) surface.
Figure 16:
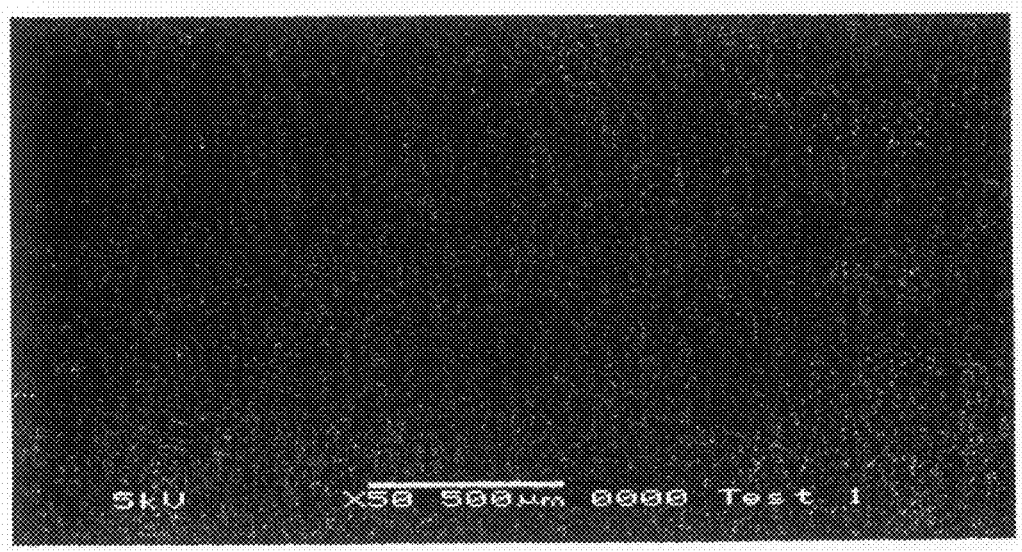
FIG. 16 is SEM image of HA adlayer on the surface of CP titanium (ASTM F67)
Figure 17:
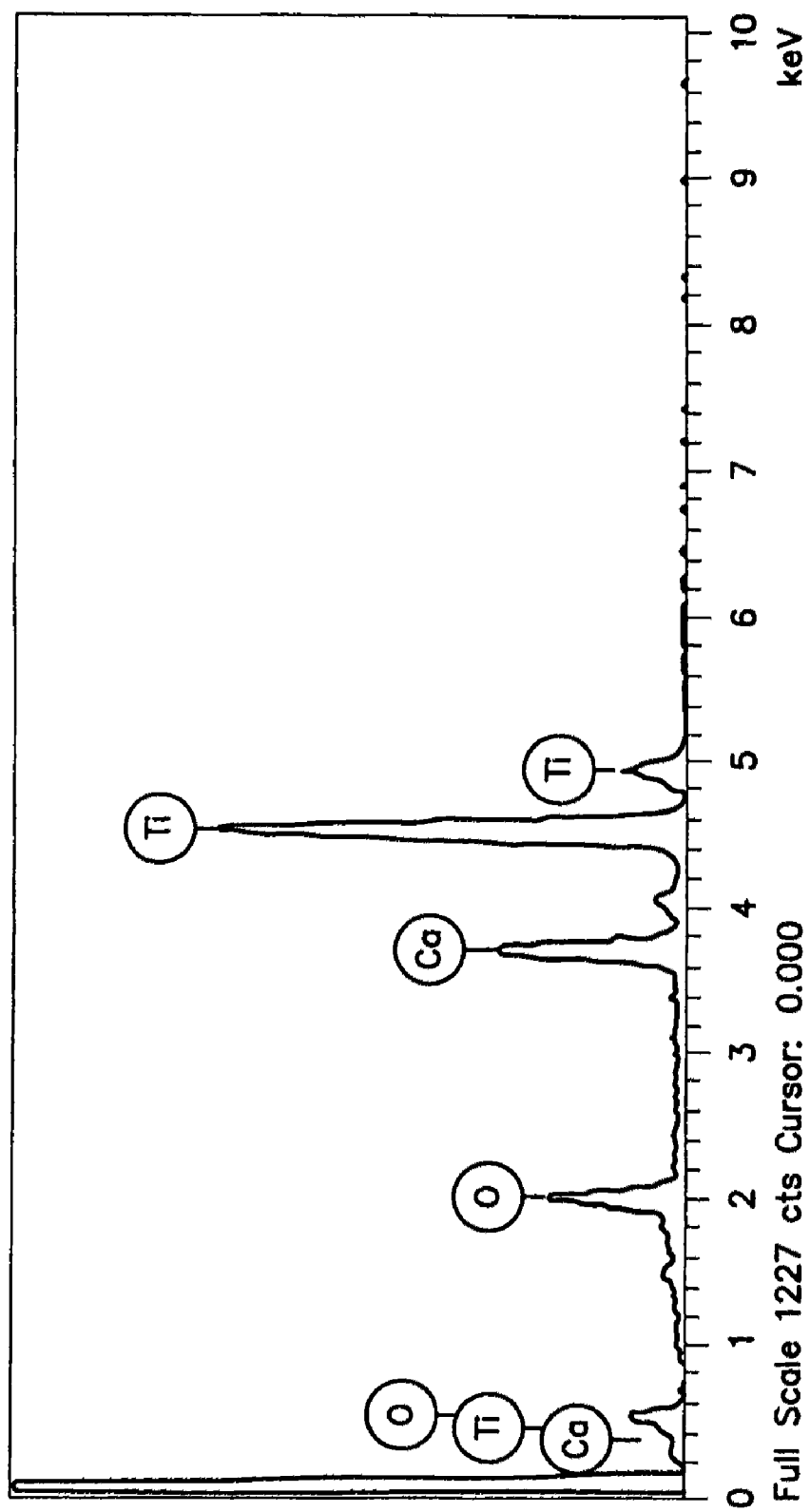
FIG. 17 is EDX spectrum for HA on CP titanium (ASTM F67) surface.
Figure 18A:
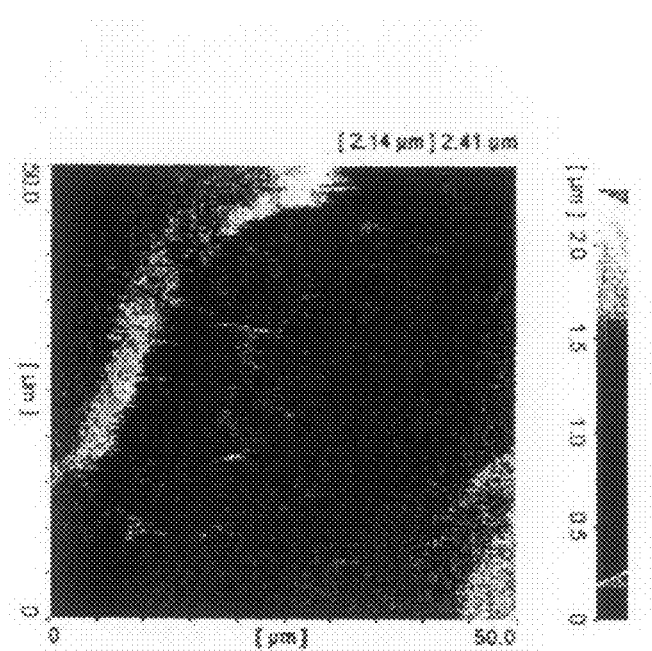
FIG. 18A is an AFM image and FIG. 18B is the corresponding AFM plot.
Figure 18B:
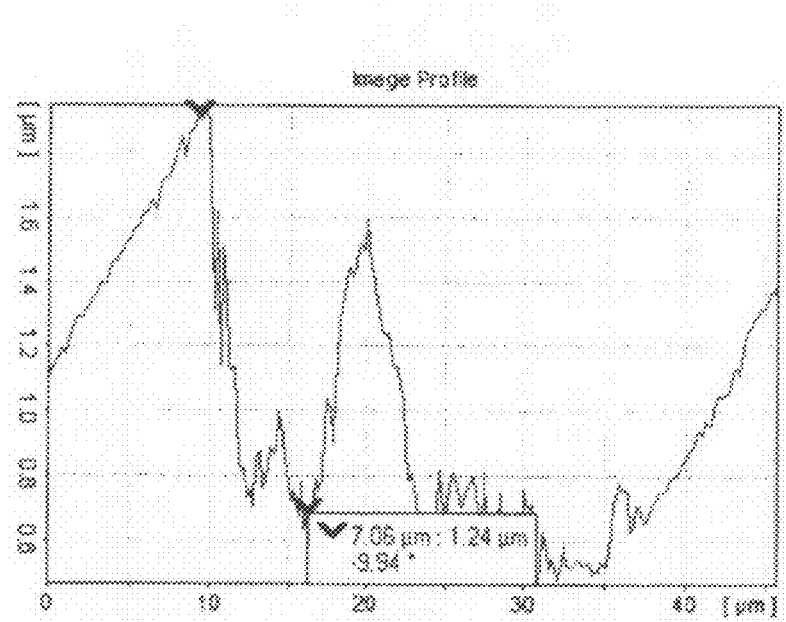

Samples were submitted for SEM/EDX (Scanning Electron Microscopy/Energy Dispersive X-Ray) analysis and AFM analysis to determine if HA was affixed to the surface of both materials. FIGS. 14 (SEM) and 15 (EDX) show a well affixed layer of HA on the surface of the stainless steel sample that gives good coverage as indicated in Table 8, with a thickness up to 6.5 microns (see FIG. 14). As expected the CP Titanium displayed an adherent layer of HA, see FIG. 16 (SEM) and FIG. 17 (EDX), while Table 9 shows the elemental analysis of the surface. FIG. 18 (AFM) shows that the affixed HA layer has a thickness of 7 microns.

TABLE 8

Elemental Analysis of the HA-Stainless Steel interface

| Element | Weight % | Atomic % |
|---|---|---|
| C | 33.19 | 43.85 |
| O | 47.78 | 47.39 |

TABLE 8-continued

Elemental Analysis of the HA-Stainless Steel interface

| Element | Weight % | Atomic % |
|---|---|---|
| Al | 2.12 | 1.25 |
| Si | 0.58 | 0.33 |
| P | 6.14 | 3.14 |
| Ca | 10.19 | 4.04 |

Ca/P = 1.28

TABLE 9

Elemental Analysis of the HA-Titanium interface

| Element | Weight % | Atomic % |
|---|---|---|
| O | 33.76 | 58.38 |
| P | 6.41 | 5.73 |
| Ca | 11.81 | 8.15 |
| Ti | 48.02 | 27.73 |

Ca/P = 1.42

Example 9

This Example describes the modification of a titanium substrate using Alumina bead as the abrasive and a nanoporous silica as the dopant. Nanoporous silica is known as a suitable drug elution carrier.

A mixed media was prepared consisting of 50 volume percent alumina (100 micron particle size, Mohs hardness 9, Comco Inc.) and 50 volume percent Mesoporous Silica (particle size is approx. 1 microns; pore size 10 nanometers, Glantreo Ltd, Cork, Ireland). A Comco MB1000 Microblaster operating at a blast pressure of 80 psi was used to grit blast nine 10 mm diameter Grade 5 titanium discs (Titanium 6AL-4V Sheet Medical to ASTM F136 Spec). The nozzle to surface distance was 15 mm and the nozzle was held at 90° to the surface. The HP (high performance) nozzle used had an orifice diameter of 0.060 inch and traversed the surface at 3.175 mm sec-1. The surface was subjected to one pass through the centre of each metal disc.

The samples were then subjected to a cleaning treatment involving 20 minutes ultrasonic washing in deionized water to remove any material that was not intimately affixed to the surface. After the ultrasonic cleaning the samples were rinsed with deionized water and air-dried in an oven at 40° C. for one hour.

Figure 19:
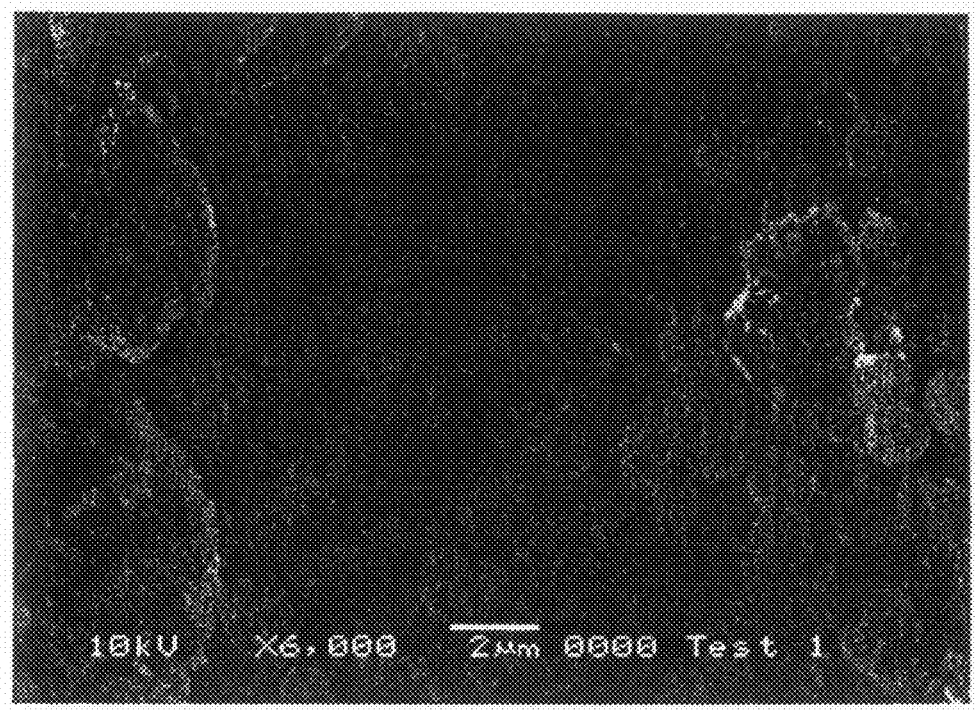
FIG. 19 is an SEM image of $SiO_2$ nanoporous microparticles on the surface of Grade 5 Titanium (Ti6AL-4V to ASTM F136)

Samples were submitted for SEM (Scanning Electron Microscopy) analysis to determine the presence of the Silica micro-particles on the surface of the Grade 5 Titanium. FIG. 19 displays the Silica particles affixed to the surface.

Example 10

This Example describes the modification of aluminum and nitinol substrates with nanoporous HA (a drug elution carrier) as a dopant and alumina bead as an abrasive.

A mixed media was prepared consisting of 90 weight percent alumina (White Saftigrit: Mesh size 150, 88 micron particle size, Mohs hardness 9, Guyson international Ltd) and 10 weight percent nanoporous HA (particle size average 50 Microns; irregular non-spherical particles; pore size 3-4 nanometers, Glantreo Ltd, Cork, Ireland). A Rocatec™ grit blaster operating at a pressure of 5 bar was used to grit blast Aluminum and Nitinol. The nozzle to surface distance was 0.5 cm and the nozzle was held at 900 to the surface. The silicon carbide nozzle had an orifice diameter of 1 mm and traversed the surface at 2 cm sec-1. The surfaces were subjected to three passes.

The samples were then subjected to a cleaning treatment involving 20 minutes ultrasonic washing in deionized water to remove any material that was not intimately affixed to the surface. After the ultrasonic cleaning the samples were rinsed with deionized water and air-dried in an oven at 40° C. for one hour.

Figure 20A:
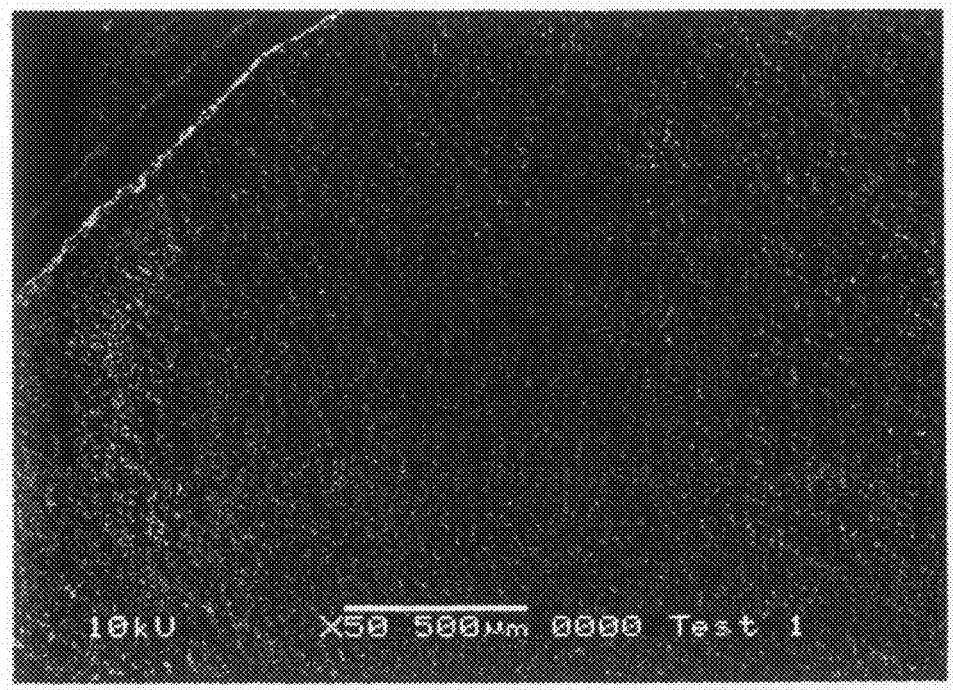
FIGS. 20A and 20B are SEM images of nanoporous HA adlayer on the surface of aluminium at a magnification of ×50 (20A) and ×650 (20B)
Figure 20B:
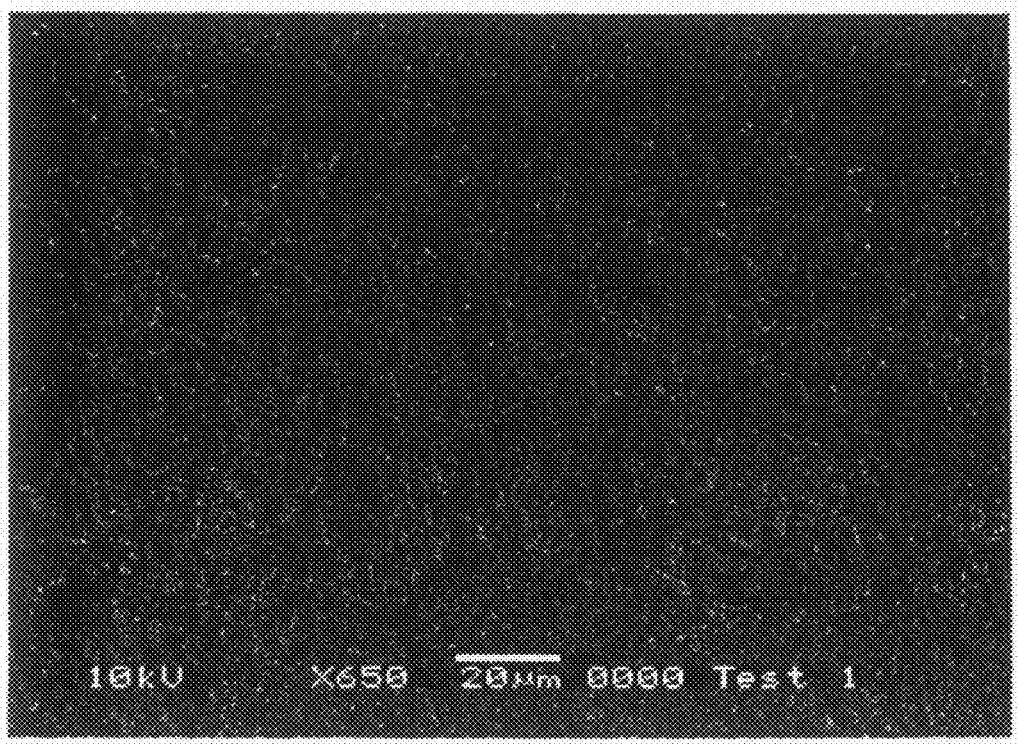
Figure 21:
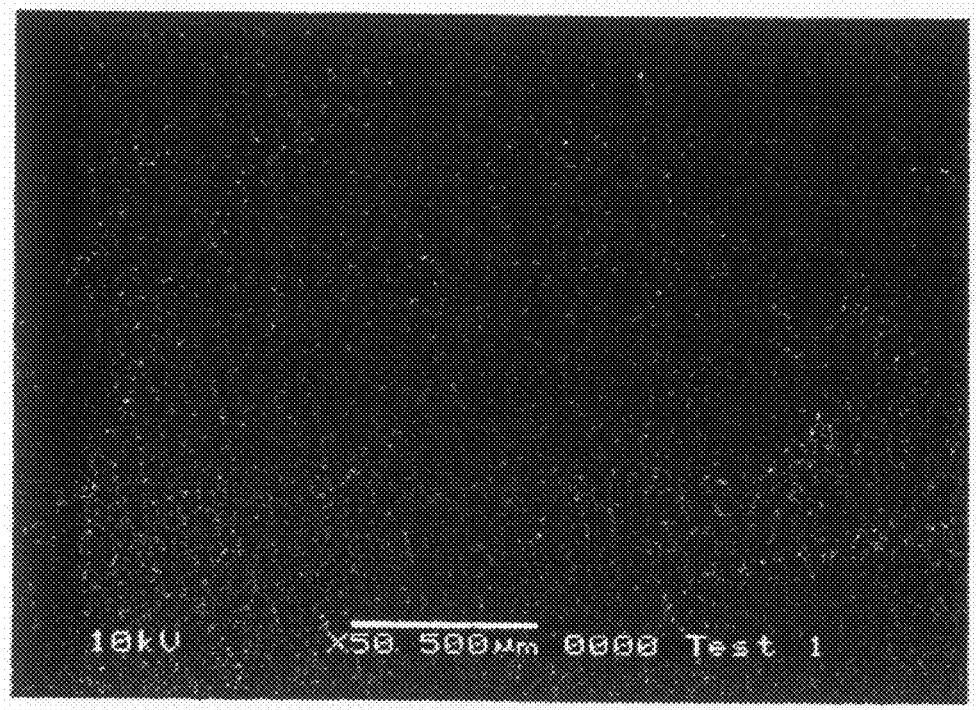
FIG. 21 an SEM image of nanoporous HA adlayer on the surface of nitinol.

Samples were submitted for SEM (Scanning Electron Microscopy) analysis to determine the presence of the Nanoporous HA on the aluminum and nitinol surfaces. FIGS. 20A and 20B are SEM images of the nanoporous HA adlayer on the aluminum surface, and FIG. 21 is a SEM image of the nanoporous HA adlayer on the nitinol surface.

The invention claimed is:

1. A method of treating a metal substrate, comprising:
removing, by abrasively blasting, a metal oxide from a surface of the metal substrate to expose a metal surface; and
delivering particles comprising a dopant from at least one fluid jet to the metal surface to impregnate the surface of the substrate with the dopant, wherein the metal substrate forms at least part of an implantable medical device.

2. A method as claimed in claim 1, wherein the removing is performed under an inert atmosphere.

3. A method as claimed in claim 1, wherein the removing is performed substantially simultaneously with the delivering such that the metal surface is not substantially oxidized prior to the delivering.

4. A method as claimed in claim 1, wherein the step of abrasively blasting is selected from grit blasting, micro blasting, water jet blasting, and shot peening.

5. A method as claimed in claim 1, wherein the step of abrasively blasting is performed simultaneously with the step of delivering the particles comprising the dopant.

6. A method as claimed in claim 1, wherein the substrate is selected from titanium, stainless steel, aluminium, and nitinol.

7. A method as claimed in claim 1, wherein the at least one fluid jet is from wet blasters.

8. A method as claimed in claim 7, wherein the at least one fluid jet operates at a pressure ranging from 0.5 to 100 bar.

9. A method as claimed in claim 7, wherein the at least one fluid jet operates at a pressure ranging from 1 to 30 bar.

10. A method as claimed in claim 7, wherein the at least one fluid jet operates at a pressure ranging from 1 to 10 bar.

11. A method as claimed in claim 1, wherein the at least one fluid jet is selected from dry blasters, grit blasters, sand blasters(s), and micro-blasters.

12. A method as claimed in claim 11, wherein the at least one fluid jet operates at a pressure ranging from 0.5 to 100 bar.

13. A method as claimed in claim 11, wherein the at least one fluid jet operates at a pressure ranging from 1 to 30 bar.

14. A method as claimed in claim 11, wherein the at least one fluid jet operates at a pressure ranging from 3 to 10 bar.

15. A method as claimed in claim 1, wherein the metal substrate is chosen from pure metals, metal alloys, intermetals comprising single or multiple phases, intermetals comprising amorphous phases, intermetals comprising single crystal phases, and intermetals comprising polycrystalline phases.

16. A method as claimed in claim 1, wherein the metal substrate is selected from titanium, titanium alloys, ferrous alloys, stainless steel, stainless steel alloys, carbon steel, carbon steel alloys, aluminum, aluminum alloys, nickel, nickel alloys, nickel titanium alloys, tantalum, tantalum alloys, niobium, niobium alloys, chromium, chromium alloys, cobalt, cobalt alloys, precious metals, and precious metal alloys.

17. A method as claimed in claim 1, wherein the metal substrate is selected from titanium, aluminum, stainless steel, and nitinol.

18. A method as claimed in claim 1, wherein the implantable medical device is selected from a catheter, guide wires, and baskets used in the removal of pathological calcifications.

19. A method as claimed in claim 1, wherein the particles are delivered in a gaseous carrier fluid.

20. A method as claimed in claim 19, wherein the carrier fluid is selected from nitrogen, hydrogen, argon, helium, air, ethylene oxide, and combinations thereof.

21. A method as claimed in claim 1, wherein the particles are delivered in a liquid carrier fluid.

22. A method as claimed in claim 21, wherein the liquid is also an etching liquid.

23. A method as claimed in claim 22, wherein the etching liquid is basic.

24. A method as claimed in claim 22, wherein the etching liquid is acidic.

25. A method as claimed in claim 1, wherein the delivering is carried out in an inert environment.

26. A method as claimed in claim 1, wherein the abrasively blasting is performed with an abrasive selected from silica, alumina, zirconia, barium titanate, calcium titanate, sodium titanate, titanium oxide, glass, biocompatible glass, diamond, silicon carbide, calcium phosphate, calcium carbonate, metallic powders, metallic wires, carbon fiber composites, polymers, polymeric composites, titanium, stainless steel, hardened steel, chromium alloys.

27. A method as claimed in claim 1, wherein the abrasively blasting is performed with an abrasive having a mohs hardness ranging from 0.1 to 10.

28. A method as claimed in claim 27, wherein the abrasive has a mohs hardness ranging from 1 to 10.

29. A method as claimed in claim 27, wherein the abrasive has a mohs hardness ranging from 5 to 10.

30. A method as claimed in claim 1, wherein the abrasively blasting is performed with an abrasive having a particle size ranging from 0.1 μm to 10000 μm.

31. A method as claimed in claim 30, wherein the abrasive has a particle size ranging from 1 μm to 5000 μm.

32. A method as claimed in claim 30, wherein the abrasive has a particle size ranging from 10 μm to 1000 μm.

33. A method as claimed in claim 1, wherein the dopant is selected from polymers, metals, ceramics and combinations thereof.

34. A method as claimed in claim 1, wherein the dopant comprises two or more different materials.

35. A method as claimed in claim 1, wherein the dopant is a metal oxide.

36. A method as claimed in claim 1, wherein the dopant is selected from barium titanate, calcium titanate, sodium titanate, zeolite, silaceous zeolite, zeolites containing phosphorous, silica, alumina, zirconia, calcium carbonate, biocompatible glass, calcium phosphate glass, and titanium dioxide.

37. A method as claimed in claim 1, wherein the dopant is an osteoconductive or osteointegrative agent.

38. A method as claimed in claim 37, wherein the osteoconductive or osteointegrative agent is a modified calcium phosphate.

39. A method as claimed in claim 37, wherein the osteoconductive or osteointegrative agent is selected from $Ca_5(PO_4)_3OH$, $CaHPO_42H_2O$, $CaHPO_4$, $Ca_8H_2(PO_4)_65H_2O$, $\alpha\text{-}Ca_3(PO_4)_2$, and combinations thereof.

40. A method as claimed in claim 38, wherein the modified calcium phosphate contains at least one anion selected from carbonate, chloride, fluoride, silicate and aluminate.

41. A method as claimed in claim 38, wherein the modified calcium phosphate contains at least one cation selected from protons, potassium, sodium, magnesium, barium and strontium.

42. A method as claimed in claim 1, wherein the dopant is a therapeutic agent.

43. A method as claimed in claim 42, wherein the therapeutic agent is immobilized on or in a carrier material.

44. A method as claimed in claim 43, wherein the carrier material is selected from polymers, calcium phosphate, titanium dioxide, silica, biopolymers, biocompatible glasses, zeolite, demineralised bone, de-proteinated bone, allograft bone, and composite combinations thereof.

45. A method as claimed in claim 44, wherein the polymers are selected from polyurethanes, polyethylene terephthalate, PLLA-poly-glycolic acid (PGA) copolymer (PLGA), poly-caprolactone, poly-(hydroxybutyrate/hydroxyvalerate) copolymer, poly(vinylpyrrolidone), polytetrafluoroethylene, poly(2-hydroxyethylmethacrylate), poly(etherurethane urea), silicones, acrylics, epoxides, polyesters, urethanes, parlenes, polyphosphazene polymers, fluoropolymers, polyamides, polyolefins, and blends and copolymers thereof.

46. A method as claimed in claim 44, wherein the biopolymers are selected from polysaccharides, gelatin, collagen, alginate, hyaluronic acid, alginic acid, carrageenan, chondroitin, pectin, chitosan, and derivatives, blends and copolymers thereof.

47. A method as claimed in claim 42, wherein the therapeutic agent is selected from anti-cancer drugs, anti-inflammatory drugs, immunosuppressants, antibiotics, heparin, functional proteins, a regulatory protein, structural proteins, oligo-peptides, antigenic peptides, nucleic acids, immunogens, and combinations thereof.

48. A method as claimed in claim 47, wherein the anticancer drugs are selected from acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, Bacillus calmette-guerin (BCG), Baker's Antifol (soluble), beta-2'-deoxythioguanosine, bisantrene HCl, bleomycin sulfate, busulfan, buthionine sulfoximine, BWA 773U82, BW 502U83.HCl, BW 7U85 mesylate, ceracemide, carbetimer, carboplatin, carmustine, chlorambucil, chloroquinoxaline-sulfonamide, chlorozotocin, chromomycin A3, cisplatin, cladribine, corticosteroids, Corynebacterium parvum, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, edatrexate, edelfosine, eflornithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, Fluosol., flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, interferon alfa, interferon beta, interferon gamma, interleukin-1 alpha and beta, interleukin-3, interleukin-4, interleukin-6, 4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of Bacillus calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864, zorubicin, and mixtures thereof.

49. A method as claimed in claim 47, wherein the anti-inflammatory drugs are selected from non-steroidal anti-inflammatory drugs, COX-2 inhibitors, glucocorticoids, and mixtures thereof.

50. A method as claimed in claim 49, wherein the non-steroidal anti-inflammatory drugs are selected from aspirin, diclofenac, indomethacin, sulindac, ketoprofen, flurbiprofen, ibuprofen, naproxen, piroxicam, tenoxicam, tolmetin, ketorolac, oxaprosin, mefenamic acid, fenoprofen, nambumetone, acetaminophen, and mixtures thereof.

51. A method as claimed in claim 49, wherein the COX-2 inhibitors are selected from nimesulide, NS-398, flosulid, L-745337, celecoxib, rofecoxib, SC-57666, DuP-697, parecoxib sodium, JTE-522, valdecoxib, SC-58125, etoricoxib, RS-57067, L-748780, L-761066, APHS, etodolac, meloxicam, S-2474, and mixtures thereof.

52. A method as claimed in claim 49, wherein the glucocorticoids are selected from such as hydrocortisone, cortisone, prednisone, prednisolone, methylprednisolone, mepredisone, triamcinolone, paramethasone, fluprednisolone, betamethasone, dexamethasone, fludrocortisone, desoxycorticosterone, and mixtures thereof.

53. A method as claimed in claim 47, wherein the antibiotics are chosen from tobramycin, vancomycin, gentamicin, ampicillin, penicillin, cephalosporin C, cephalexin, cefaclor, cefamandole and ciprofloxacin, and mixtures thereof.

54. A method according to claim 47, wherein the proteins are chosen from albumin, casein, gelatin, lysosime, fibronectin, fibrin, chitosan, polylysine, polyalanine, polycysteine, Bone Morphogenetic Protein (BMP), Epidermal Growth Factor (EGF), Fibroblast Growth Factor (bFGF), Nerve Growth Factor (NGF), Bone Derived Growth Factor (BDGF), Transforming Growth Factor-β1 (TGF-β1), Transforming Growth Factor-β (TGF-β), the tri-peptide arginine-glycine-aspartic acid (RGD), vitamin D3, dexamethasone, and human Growth Hormone (hGH), epidermal growth factors, transforming growth factor α, transforming growth factor β, vaccinia growth factors, fibroblast growth factors, insulin-like growth factors, platelet derived growth factors, cartilage derived growth factors, interlukin-2, nerve cell growth factors, hemopoietic cell growth factors, lymphocyte growth factors, bone morphogenic proteins, osteogenic factors, chondrogenic factors, or and mixtures thereof.

55. A method as claimed in claim 47, wherein the heparin is selected from recombinant heparin, heparin derivatives, and heparin analogues or combinations thereof.

56. A method as claimed in claim 47, wherein the oligo-peptide is a bactericidal oligo-peptide.

57. A method as claimed in claim 47, wherein the immunogen is a viral antigen, a bacterial antigen, a fungal antigen, a parasitic antigen, tumor antigens, a peptide fragment of a tumor antigen, meta static specific antigens, a passive or active vaccine, a synthetic vaccine or a subunit vaccine.

58. A method as claimed in claim 1, wherein the dopant is a radio opaque material.

59. A method as claimed in claim 58, wherein the radio opaque material is chosen from alkalis earth metals, transition metals, rare earth metals, and oxides, sulphates, phosphates and combinations thereof.

60. A method as claimed in claim 58, wherein the radio-opaque material is a polymer.

61. A method of treating a metal substrate surface, the method comprising:
removing, by abrasively blasting, a metal oxide from the surface of the metal substrate to expose a metal surface; and
delivering substantially simultaneously a first set of particles comprising a dopant and a second set of particles comprising an abrasive from at least one fluid jet to the surface of the metal substrate to impregnate the surface of the metal with the dopant, wherein the metal substrate forms at least part of an implantable medical device.

62. A method as claimed in claim 61, wherein the at least one fluid jet is from wet blasters.

63. A method as claimed in claim 61, wherein the at least one fluid jet is selected from dry blasters, grit blasters, sand blasters(s), and micro-blasters.

64. A method as claimed in claim 62, wherein the at least one fluid jet operates at a pressure ranging from 0.5 to 100 bar.

65. A method as claimed in claim 62 wherein the at least one fluid jet operates at a pressure ranging from 1 to 30 bar.

66. A method as claimed in claim 62, wherein the at least one fluid jet operates at a pressure ranging from 1 to 10 bar.

67. A method as claimed in claim 63, wherein the at least one fluid jet operates at a pressure ranging from 0.5 to 100 bar.

68. A method as claimed in claim 63, wherein the at least one fluid jet operates at a pressure ranging from 1 to 30 bar.

69. A method as claimed in claim 63, wherein the at least one fluid jet operates at a pressure ranging from 3 to 10 bar.

70. A method as claimed in claim 61, wherein the metal substrate is chosen from pure metals, metal alloys, intermetals comprising single or multiple phases, intermetals comprising amorphous phases, intermetals comprising singe crystal phases, and intermetals comprising polycrystalline phases.

71. A method as claimed in claim 61, wherein the metal substrate is selected from titanium, titanium alloys, ferrous alloys, stainless steel, stainless steel alloys, carbon steel, carbon steel alloys, aluminum, aluminum alloys, nickel, nickel alloys, nickel titanium alloys, tantalum, tantalum alloys, niobium, niobium alloys, chromium, chromium alloys, cobalt, cobalt alloys, precious metals, and precious metal alloys.

72. A method as claimed in claim 61, wherein the metal substrate is selected from titanium, aluminum, stainless steel, and nitinol.

73. A method as claimed in claim 61, wherein the implantable medical device is selected from a catheter, guide wires, and baskets used in the removal of pathological calcifications.

74. A method as claimed in claim 61, wherein the first and second particles are delivered in a gaseous carrier fluid.

75. A method as claimed in claim 74, wherein the carrier fluid is selected from nitrogen, hydrogen, argon, helium, air, ethylene oxide, and combinations thereof.

76. A method as claimed in claim 61, wherein the first and second particles are delivered in a liquid carrier fluid.

77. A method as claimed in claim 76, wherein the liquid is also an etching liquid.

78. A method as claimed in claim 77, wherein the etching liquid is basic.

79. A method as claimed in claim 77, wherein the etching liquid is acidic.

80. A method as claimed in claim 61, wherein the delivering is carried out in an inert environment.

81. A method as claimed in claim 61, wherein the abrasive is selected from silica, alumina, zirconia, barium titanate, calcium titanate, sodium titanate, titanium oxide, glass, biocompatible glass, diamond, silicon carbide, calcium phosphate, calcium carbonate, metallic powders, metallic wires, carbon fiber composites, polymers, polymeric composites, titanium, stainless steel, hardened steel, chromium alloys.

82. A method as claimed in claim 61, wherein the abrasive has a mohs hardness ranging from 0.1 to 10.

83. A method as claimed in claim 61, wherein the abrasive has a mohs hardness ranging from 1 to 10.

84. A method as claimed in claim 61, wherein the abrasive has a mohs hardness ranging from 5 to 10.

85. A method as claimed in claim 61, wherein the abrasive has a particle size ranging from 0.1 μm to 10000 μm.

86. A method as claimed in claim 61, wherein the abrasive has a particle size ranging from 1 μm to 5000 μm.

87. A method as claimed in claim 61, wherein the abrasive has a particle size ranging from 10 μm to 1000 μm.

88. A method as claimed in claim 61, wherein the dopant is selected from polymers, metals, ceramics and combinations thereof.

89. A method as claimed in claim 61, wherein the dopant comprises two or more different materials.

90. A method as claimed in claim 61, wherein the dopant is a metal oxide.

91. A method as claimed in claim 61, wherein the dopant is selected from barium titanate, calcium titanate, sodium titanate, zeolite, silaceous zeolite, zeolites containing phosphorous, silica, alumina, zirconia, calcium carbonate, biocompatible glass, calcium phosphate glass, and titanium dioxide.

92. A method as claimed in claim 61, wherein the dopant is an osteoconductive or osteointegrative agent.

93. A method as claimed in claim 92, wherein the osteoconductive or osteointegrative agent is a modified calcium phosphate.

94. A method as claimed in claim 92, wherein the osteoconductive or osteointegrative agent is selected from $Ca_5(PO_4)_3OH$, $CaHPO_4 \cdot 2H_2O$, $CaHPO_4$, $Ca_8H_2(PO_4)_6 \cdot 5H_2O$, $\alpha\text{-}Ca_3(PO_4)_2$, $\beta\text{-}Ca_3(PO_4)_2$, and combinations thereof.

95. A method as claimed in claim 93, wherein the modified calcium phosphate contains at least one anion selected from carbonate, chloride, fluoride, silicate and aluminate.

96. A method as claimed in claim 93, wherein the modified calcium phosphate contains at least one cation selected from protons, potassium, sodium, magnesium, barium and strontium.

97. A method as claimed in claim 61, wherein the dopant is a therapeutic agent.

98. A method as claimed in claim 97, wherein the therapeutic agent is immobilized on or in a carrier material.

99. A method as claimed in claim 98, wherein the carrier material is selected from polymers, calcium phosphate, titanium dioxide, silica, biopolymers, biocompatible glasses, zeolite, demineralised bone, de-proteinated bone, allograft bone, and composite combinations thereof.

100. A method as claimed in claim 99, wherein the polymers are selected from polyurethanes, polyethylene terephthalate, PLLA-poly-glycolic acid (PGA) copolymer (PLGA), polycaprolactone, poly-(hydroxybutyrate/hydroxyvalerate) copolymer, poly(vinylpyrrolidone), polytetrafluoroethylene, poly(2-hydroxyethylmethacrylate), poly(etherurethane urea), silicones, acrylics, epoxides, polyesters, urethanes, parlenes, polyphosphazene polymers, fluoropolymers, polyamides, polyolefins, and blends and copolymers thereof.

101. The method as claimed in claim 99 wherein the biopolymers are selected from polysaccharides, gelatin, collagen, alginate, hyaluronic acid, alginic acid, carrageenan, chondroitin, pectin, chitosan, and derivatives, blends and copolymers thereof.

102. A method as claimed in claim 98, wherein the therapeutic agent is selected from anti-cancer drugs, anti-inflammatory drugs, immunosuppressants, an antibiotic, heparin, a functional protein, a regulatory protein, structural proteins, oligo-peptides, antigenic peptides, nucleic acids, immunogens, and combinations there of.

103. A method as claimed in claim 102, wherein the anti-cancer drugs are selected from acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *Bacillus* calmette-guerin (BCG), Baker's Antifol (soluble), beta-2'-deoxythioguanosine, bisantrene HCl, bleomycin sulfate, busulfan, buthionine sulfoximine, BWA 773U82, BW 502U83.HCl, BW 7U85 mesylate, ceracemide, carbetimer, carboplatin, carmustine, chlorambucil, chloroquinoxalinesulfonamide, chlorozotocin, chromomycin A3, cisplatin, cladribine, corticosteroids, *Corynebacterium parvum*, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, edatrexate, edelfosine, eflornithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, Fluosol, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, interferon alfa, interferon beta, interferon gamma, interleukin-1 alpha and beta, interleukin-3, interleukin-4, interleukin-6, 4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of *Bacillus* calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864, zorubicin, and mixtures thereof.

104. A method as claimed in claim 102, wherein the anti-inflammatory drugs are selected from non-steroidal anti-inflammatory drugs, COX-2 inhibitors, glucocorticoids, and mixtures thereof.

105. A method as claimed in claim 104, wherein the non-steroidal anti-inflammatory drugs are selected from aspirin, diclofenac, indomethacin, sulindac, ketoprofen, flurbiprofen, ibuprofen, naproxen, piroxicam, tenoxicam, tolmetin, ketorolac, oxaprosin, mefenamic acid, fenoprofen, nambumetone, acetaminophen, and mixtures thereof.

106. A method as claimed in claim 104, wherein the COX-2 inhibitors are selected from nimesulide, NS-398, flosulid, L-745337, celecoxib, rofecoxib, SC-57666, DuP-697, parecoxib sodium, JTE-522, valdecoxib, SC-58125, etoricoxib, RS-57067, L-748780, L-761066, APHS, etodolac, meloxicam, S-2474, and mixtures thereof.

107. A method as claimed in claim 104, wherein the glucocorticoids are selected from such as hydrocortisone, cortisone, prednisone, prednisolone, methylprednisolone, meprednisone, triamcinolone, paramethasone, fluprednisolone, betamethasone, dexamethasone, fludrocortisone, desoxycorticosterone, and mixtures thereof.

108. A method as claimed in claim 102, wherein the antibiotics are chosen from tobramycin, vancomycin, gentamicin, ampicillin, penicillin, cephalosporin C, cephalexin, cefaclor, cefamandole and ciprofloxacin, and mixtures thereof.

109. A method according to claim 102, wherein the proteins are chosen from albumin, casein, gelatin, lysosime, fibronectin, fibrin, chitosan, polylysine, polyalanine, polycysteine, Bone Morphogenetic Protein (BMP), Epidermal Growth Factor (EGF), Fibroblast Growth Factor (bFGF), Nerve Growth Factor (NGF), Bone Derived Growth Factor (BDGF), Transforming Growth Factor-β1 (TGF-β1), Transforming Growth Factor-β (TGF-β), the tri-peptide arginine-glycine-aspartic acid (RGD), vitamin D3, dexamethasone, and human Growth Hormone (hGH), epidermal growth factors, transforming growth factor α, transforming growth factor β, vaccinia growth factors, fibroblast growth factors, insulin-like growth factors, platelet derived growth factors, cartilage derived growth factors, interlukin-2, nerve cell growth factors, hemopoietic cell growth factors, lymphocyte growth factors, bone morphogenic proteins, osteogenic factors, chondrogenic factors, or and mixtures thereof.

110. A method as claimed in claim 102, wherein the heparin is selected from recombinant heparin, heparin derivatives, and heparin analogues or combinations thereof.

111. A method as claimed in claim 102, wherein the oligo-peptide is a bactericidal oligo-peptide.

112. A method as claimed in claim 102, wherein the immunogen is a viral antigen, a bacterial antigen, a fungal antigen, a parasitic antigen, tumor antigens, a peptide fragment of a tumor antigen, meta static specific antigens, a passive or active vaccine, a synthetic vaccine or a subunit vaccine.

113. A method as claimed in claim 61, wherein the dopant is a radio opaque material.

114. A method as claimed in claim 113, wherein the radio opaque material is chosen from alkalis earth metals, transition metals, rare earth metals, and oxides, sulphates, phosphates and combinations thereof.

115. A method as claimed in claim 113, wherein the radio-opaque material is a polymer.

116. A method as claimed in claim 61, wherein the first and second set of particles are delivered to the surface from the same fluid jet.

117. A method as claimed in claim 61, wherein the first and second set of particles are delivered to the surface from separate fluid jets.

* * * * *